United States Patent
Eidelman et al.

(10) Patent No.: US 6,822,734 B1
(45) Date of Patent: Nov. 23, 2004

(54) APPARATUS AND METHOD FOR FABRICATING FLAT WORKPIECES

(75) Inventors: Doron Eidelman, Ramat Hasharon (IL); David Fisch, Paduel (IL); Amir Noy, Kfar Mordechai (IL); Avi Gross, Ramat Aviv (IL)

(73) Assignee: Orbotech Ltd., Yavne (IL)

( * ) Notice: Subject to any disclaimer, the term of this patent is extended or adjusted under 35 U.S.C. 154(b) by 0 days.

(21) Appl. No.: 09/807,680

(22) PCT Filed: Nov. 2, 1999

(86) PCT No.: PCT/IL99/00583
§ 371 (c)(1),
(2), (4) Date: Sep. 4, 2001

(87) PCT Pub. No.: WO00/26645
PCT Pub. Date: May 11, 2000

(30) Foreign Application Priority Data

Nov. 2, 1998 (IL) .............................................. 126866

(51) Int. Cl.$^7$ ............................................. G01N 21/88
(52) U.S. Cl. .................................... 356/237.2; 356/601
(58) Field of Search ............... 356/237.1, 237.2–237.5, 356/123, 600, 601, 609, 610, 394, 445–448, 239.7, 239.8

(56) References Cited

U.S. PATENT DOCUMENTS

| | | | |
|---|---|---|---|
| 5,058,491 A | 10/1991 | Wiemer et al. ............. 98/115.3 |
| 5,058,982 A | 10/1991 | Katzir .......................... 385/33 |
| 5,333,052 A | 7/1994 | Finarov ...................... 356/369 |
| 5,344,365 A | 9/1994 | Scott .......................... 454/187 |
| 5,562,383 A | 10/1996 | Iwai et al. .................. 414/217 |
| 5,586,058 A | 12/1996 | Aloni et al. ................ 364/552 |
| 5,640,237 A | 6/1997 | Esrig et al. ................. 356/237 |
| 5,715,052 A | 2/1998 | Fujino et al. .............. 356/237 |
| 5,771,068 A | 6/1998 | Sali et al. .................... 348/92 |
| 6,362,884 B1 | 3/2002 | Okahira et al. ............. 356/399 |
| 6,654,113 B2 * | 11/2003 | Fukazawa et al. ....... 356/237.4 |

FOREIGN PATENT DOCUMENTS

| | | |
|---|---|---|
| EP | 0 196 333 | 10/1986 |
| EP | 0 672 933 | 9/1995 |
| JP | 11-94753 | 8/1989 |
| WO | WO 94/17336 | 8/1994 |
| WO | WO 98/20327 | 5/1998 |

OTHER PUBLICATIONS

Advanced Long–Range Reader (ALR) Brochure, *LAN–LINK CORP.*, St. Louis, Missouri, Jul. 1999, 3 pages.
Qcard® RFID Transponder, *LAN–LINK CORP.*, St. Louis, Missouri, Jan. 1999, 1 page.
"Supporting Realization of Double Productivity in Phase II Lines", *Trends*, 3 pages, 1996.
Catalogue, PHOTON DYNAMICS: Products and Technologies, 2 pages, 1997.

* cited by examiner

*Primary Examiner*—Richard A. Rosenberger
*Assistant Examiner*—Vincent P. Barth
(74) *Attorney, Agent, or Firm*—Ladas & Parry

(57) ABSTRACT

Method and apparatus for manufacture and inspection of flat articles, such as flat planel display substrates, that are manufactured in a contamination-sensitive environment. In particular, a manufacturing step such as applying coatings to the article is performed in a self-contained micro-environment, typically characterized by an airborn particulate concentration which is substantially lower than its surroundings. Automated inspection apparatus is provided inside the self-contained micro-environment of the fabrication equipment to inspect the article after completion of the fabrication step and before transfer of the article to other fabrication equipment. The inspection apparatus includes an illumination subsystem illuminating the article with various configurations of dark field and bright field illumination, a staring array sensor capturing images of the article under various illumination configurations and a computer that analyzes the images to automatically detect defects.

100 Claims, 23 Drawing Sheets

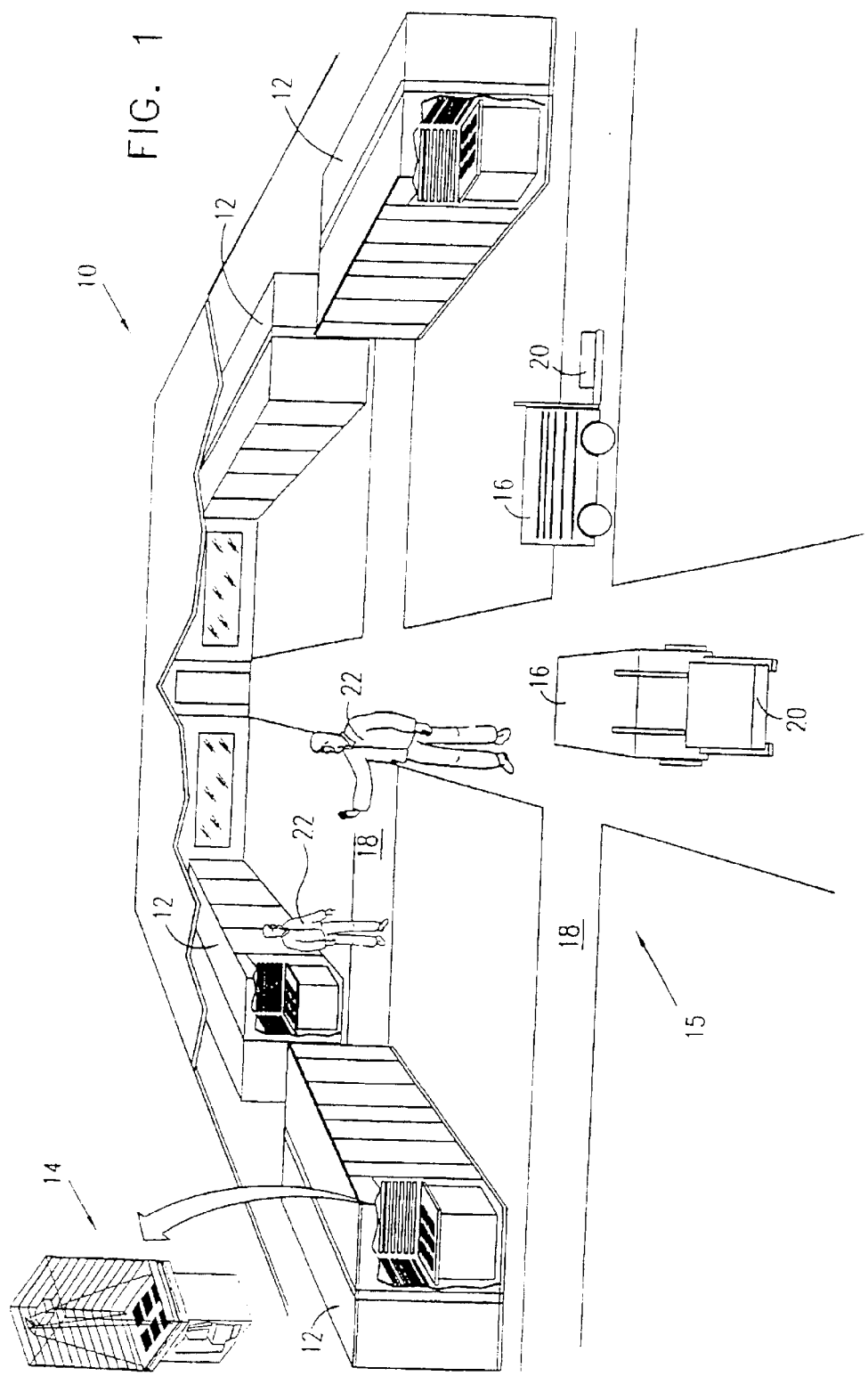

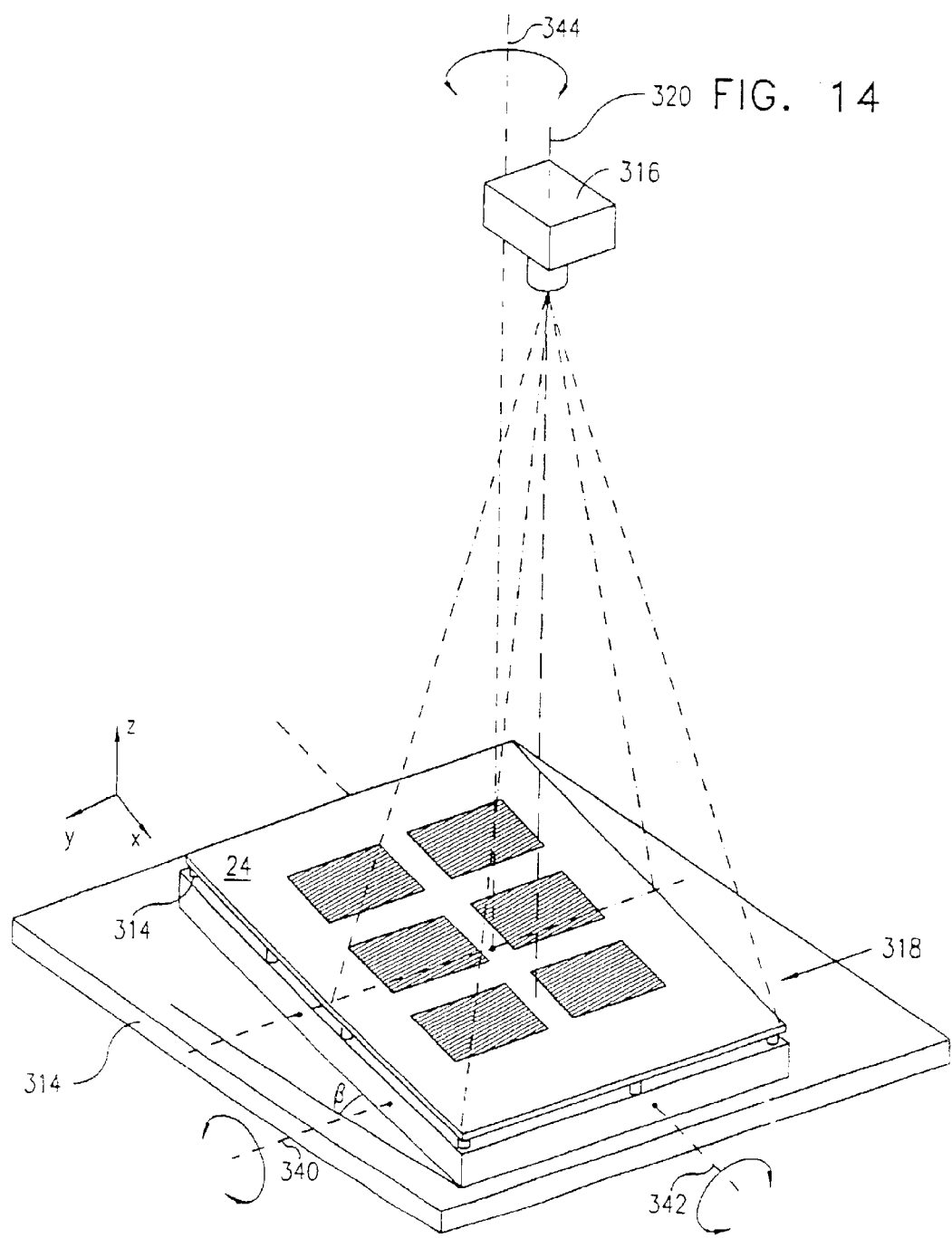

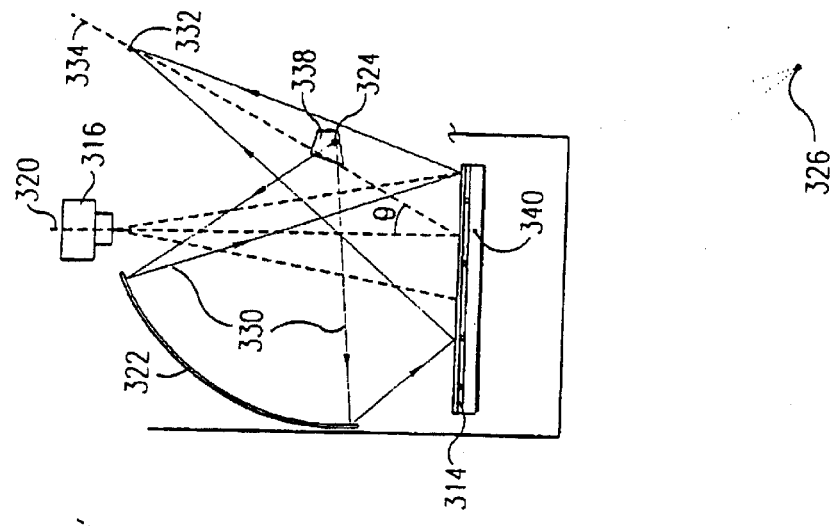
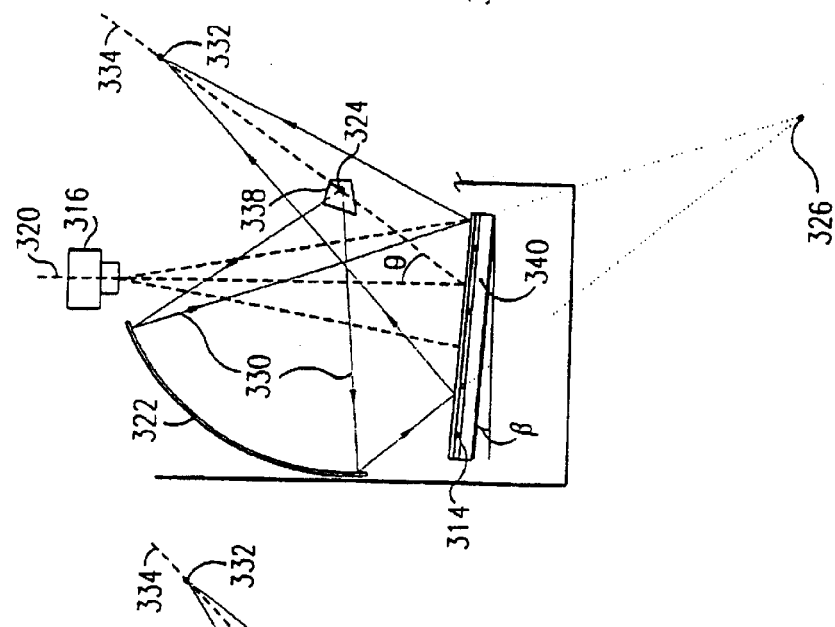
FIG. 15A  FIG. 15B  FIG. 15C

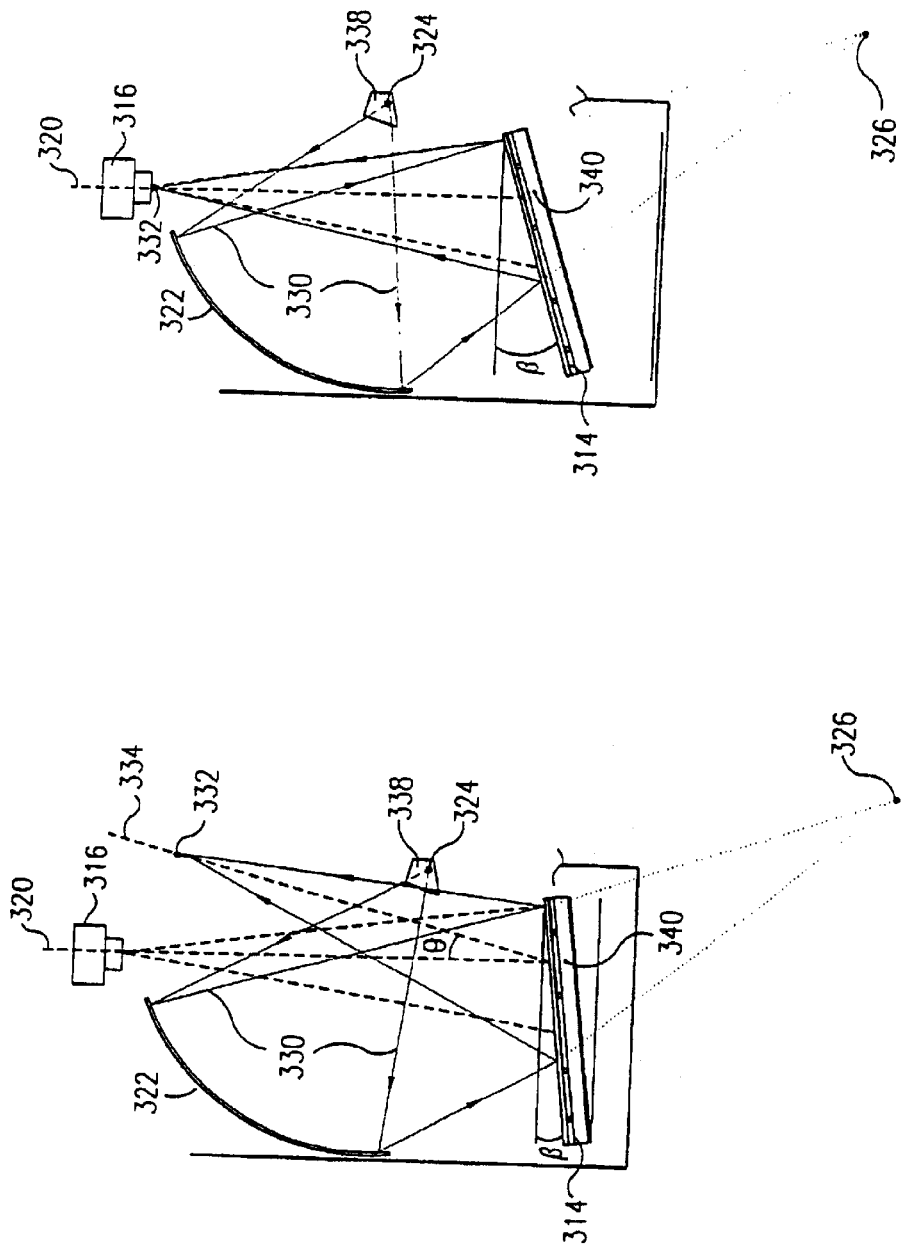

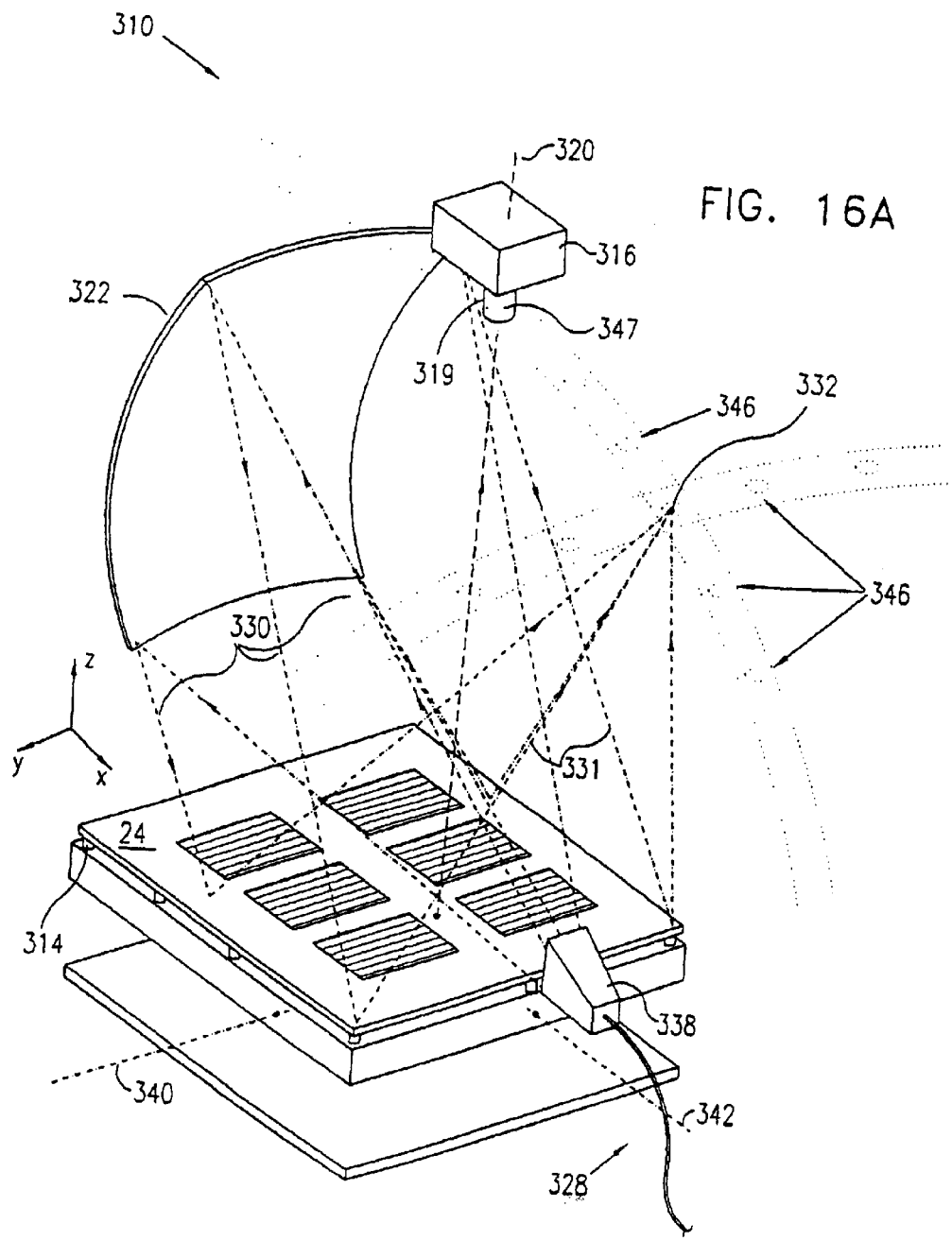

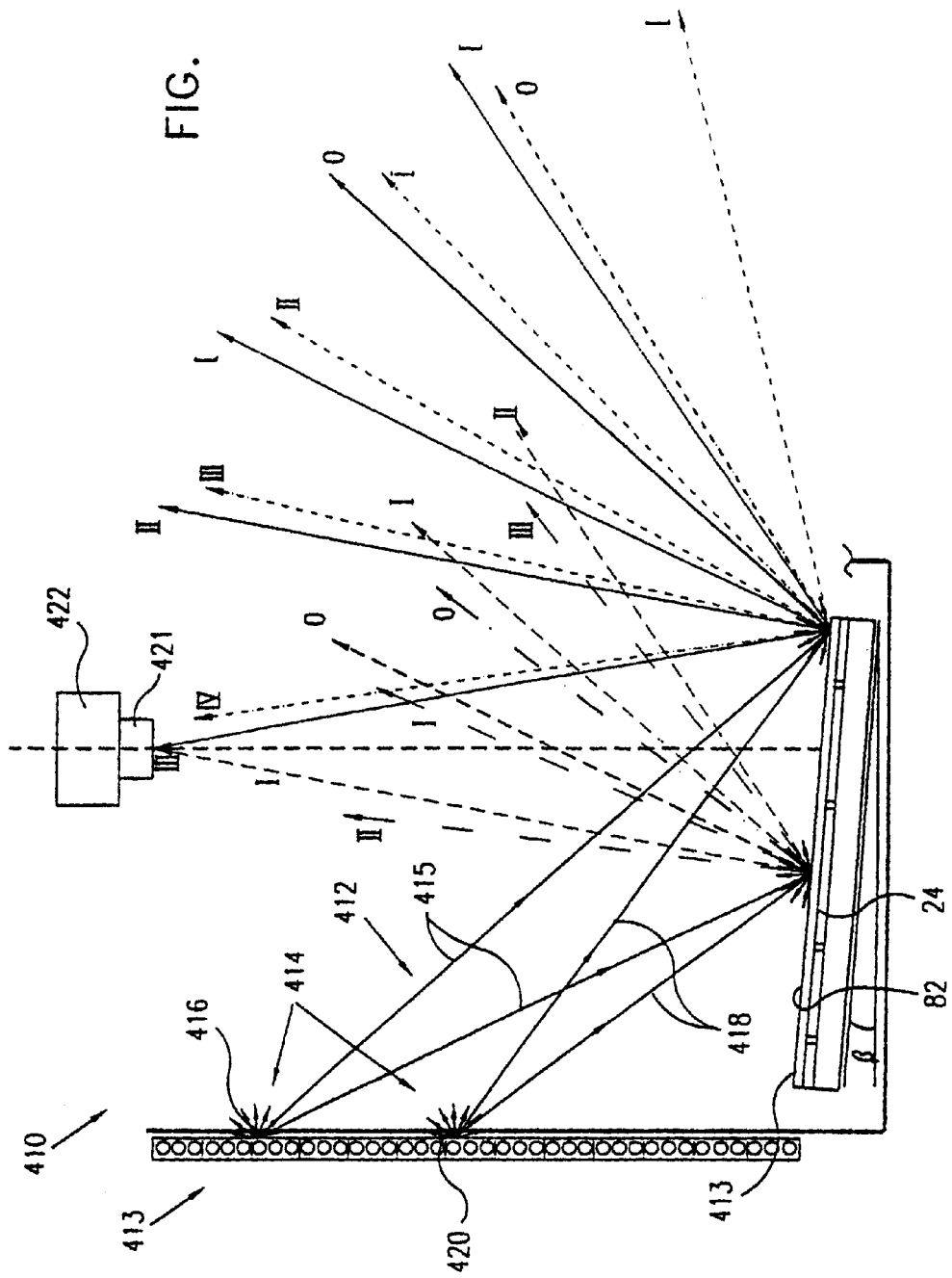

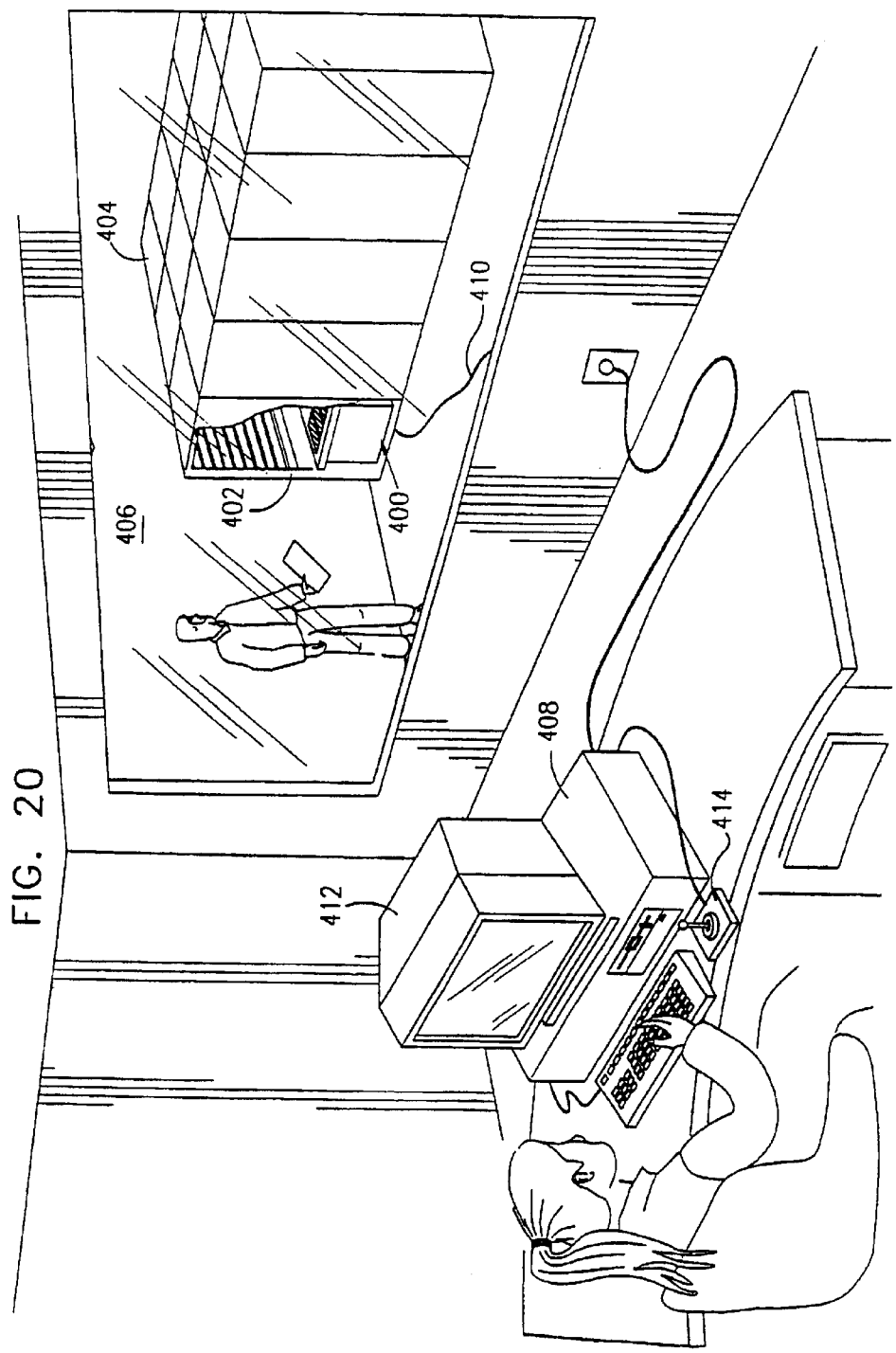

APPARATUS AND METHOD FOR FABRICATING FLAT WORKPIECES

FIELD OF INVENTION

The present invention relates to the fabrication and inspection of flat workpieces in general and more particularly to the fabrication and inspection of flat articles such as flat panel display screens (FPDs) for computers, television and other suitable applications.

BACKGROUND OF THE INVENTION

Flat panel visual displays such as liquid crystal displays (LCDS) are becoming increasingly popular for use in computer and television screens. However their cost remains high, in part, due to relatively low manufacturing yields.

There exist various well known techniques for FPD fabrication. Most of these techniques comprise a multi-step photolithographic process in which various thin films and photo-sensitive protective photoresist coatings are applied in turn to a glass substrate. The thin films may be metallic, non-metallic dielectric or the like depending on the particular process step. The photoresist coatings are selectively exposed, typically to UV light, developed and selectively washed away from the substrate. The thin films are etched to selectively remove regions not protected by residual photoresist. Repetition of this process deposits on the substrate a multi-layered matrix structure of metal connectors, thin film transistors, optical filters such as polarizors, and individually controllable liquid crystal cells.

Various steps in the FPD fabrication process are highly sensitive to airborne and other impurities as well as to process defects. Unfiltered air typically contains many millions of airborne particles, such as dust, per cubic meter. Conventional FPD fabrication techniques require that the maximum level of airborne particulate concentration range between 10–100 particles per cubic meter, depending on the sensitivity of the given process step.

Consequently, FPDs are typically fabricated in environments containing highly filtered air thus providing reduced contamination by airborne particles.

FPD fabrication facilities are typically situated in so-called "clean rooms" in which the ambient air is filtered to maintain a level of airborne particulate contamination which is at the upper end of the above-mentioned concentration range, typically at a concentration level of less than 100 airborne particles per cubic meter. This level of particulate contamination is insufficiently low for some fabrication steps. However, it is generally impracticable, because of cost and limitations on human access, to maintain large volumes of air in a clean room at the low levels of airborne particulate concentration required for such extremely contamination-sensitive fabrication steps. Consequently. FPD fabrication equipment performing steps requiring an even lower level of airborne particulate concentration typically includes a self-contained ultra clean micro-environment in which a required low level of airborne particulate concentration is maintained. Other types of FPD fabrication equipment define a micro-environment which may not differ from those of the clean room in terms of its airborne particulate concentration, but which differs in other characteristics.

In a typical FPD fabrication facility, human attendants are permitted into the clean room facilities having maximum concentration levels as low as 100 particles per cubic meter, however the attendants must be suitably dressed in protective clothing. Human attendants, even in suitable dress, typically can not access self-contained micro environments of fabrication equipment during operation thereof. Consequently, fabrication equipment operating is typically fully automated and is operational without human intervention.

It is well known to inspect FPD substrates during and following fabrication. Conventional automated inspection techniques are directed to ascertaining the uniformity of a matrix structure deposited on a glass substrate, determines whether dust has been trapped in intermediate matrix layers on the FPD, and ascertaining the performance of completed FPD panels. In addition non-automated human inspection is used to determine the existence of large scale process defects, generally visible to the human eye, such as chemical residues that have not been fully washed away, streaks, scratches and uneven exposure of the photoresist. The present invention relates to inspections of this latter type, namely large scale process defects.

Conventionally, all inspection of FPD substrates is performed in a clean room but outside the self-contained ultra-clean micro environments of the FPD fabrication equipment. A batch of substrates is typically inspected only after a series of process steps is completed. There is often a considerable time delay between the completion of a fabrication process and inspection. In the event of recurring contamination or recurring process flaws, many conventional automated system for inspecting FPD substrates during fabrication for ascertaining the uniformity of the matrix structure deposited on the glass substrate and determining whether dust has been trapped in intermediate matrix layers thereof, is commercially available from the present assignee, Orbotech Ltd. of Israel, and is designated by catalogue no. LC 3090. Part of this system is described and claimed in U.S. Patent The existing Orbotech system described above is not normally used for identifying many typical fabrication large scale process defects on FPD substrates because it collects data relating to a matrix structure having dimensions that are orders of magnitude smaller than those of typical process defects. Moreover, because the system scans the substrates, it is physically relatively large, expensive and complex to operate.

Human inspection for process defects is conventionally performed by an operator situated inside the clean room who positions a substrate under a light source to inspect it for undesired residues, streaks, scratches and other relatively large scale anomalies on the substrate. While such inspection can be useful to detect certain large scale fabrication process defects, it takes place outside the self-contained micro environment of contamination-sensitive process equipment and it suffers from the typical high cost and non-standardization associated with non-automated human inspection methods.

Other types of inspection, typified by the disclosure of U.S. Pat. No. 5,771,068, assigned to the present assignee and incorporated herein by reference, are conventionally used to inspect FPDs that are sufficiently completed to enable selective activation of pixels. According to an embodiment described in U.S. Pat. No. 5,771,068, various combinations of pixels are illuminated and a relatively low resolution staring array sensor images the entire substrate as the various combinations are illuminated. The images are analyzed for variations in intensities. This type of inspection is clearly not suitable for inspection FPD substrates in intermediate stages of fabrication.

Additional publications that are believed to be relevant to the art of inspecting for large scale defects and non-conformities on surfaces of articles include U.S. Pat. No. 5,640,237 and Japan Patent Application 11-94753.

SUMMARY OF INVENTION

The present invention seeks to overcome drawbacks of conventional FPD inspection systems and to provide an improved system and method for automated inspection of FPDs and other flat surfaces.

The present invention further seeks to provide an FPD manufacturing system having increased yield.

The present invention still further seeks to provide an automated system for inspecting FPDs which is less expensive and more compact in size than conventional automated scanning FPD inspection systems.

Additionally the present invention seeks to provide a system operative to inspect FPD substrates inside the self-contained ultra-clean micro environment of equipment performing contamination-sensitive FPD fabrication processes.

One aspect of a preferred embodiment of the invention relates to a system and method for the manufacture of FPDs using contamination-sensitive fabrication equipment having a self-contained micro environment typically, but not necessarily, characterized by an airborne particulate concentration that is substantially lower than that of its surroundings. Automated inspection apparatus is provided inside the self-contained micro environment of the process equipment and FPD substrates are inspected inside the micro environment of the fabrication equipment before transportation to other fabrication equipment to perform a downstream fabrication process.

Another aspect of a preferred embodiment of the invention relates to the inspection of FPD substrates that is performed inside fabrication equipment immediately following the completion of a series of fabrication process steps and before the substrate is transferred to other fabrication equipment to perform a subsequent series of steps. A determination of whether there exist any process defects on the substrate is made in order that the operation of the process equipment that is performing defective steps can be interrupted and corrected before a recurring defect affects subsequent substrates.

Another aspect of a preferred embodiment of the present invention relates to a system and method for FPD fabrication in which FPD substrates are inspected for typical fabrication process defects by an automated system. Preferably, the inspection is performed without comparison to an external reference. Preferably, inspection is provided to detect typical fabrication process defects including scratches, process residues, uneven exposure of photoresist, uneven deposition of films and contamination by particles embedded in the substrate.

Another aspect of a preferred embodiment of the present invention relates to a system to automatically inspect substantially flat surfaces of industrial articles, such as FPD substrates, for the existence and absence of relatively large scale process defects such as are generally visible to the human eye. Relatively large scale process defects include, by way of example only, in the context of FPD substrate inspection: uneven deposition of coatings, uneven removal of coatings, rinse residues, chemical residues, incomplete exposure of a photo-resist deposited on the substrate, scratches, lines, and particles embedded in the substrate.

Preferable, various configurations of illumination are applied to a surface under inspection, and for each configuration of illumination an image of an illuminated region on the surface is acquired using a sensor, preferably a staring array CCD sensor.

The types and configurations of illumination used in the context of preferred embodiments of the present invention generally include: Bright Field Illumination, in which a specular reflection of light from the source of illumination impinges on a lens associated with a sensor viewing the object; and Dark Field Illumination in which a specular reflection of light from the source of illumination does not impinge on a lens associated with a sensor viewing the object. Additionally the bright field and dark field illumination respectively may be diffuse or focused.

Thus for example, diffuse substantially bright field illumination or diffuse dark field illumination may be applied. Diffuse substantially bright field illumination refers to illumination in which a diffuse illumination source is used, and the mutual orientation of the surface under inspection, the illumination source and a lens associated with the sensor is such that the specular reflection of at least some of the light from the diffuse source impinges on a lens associated with the sensor. Diffuse dark field illumination refers to illumination in which a diffuse illumination source is used, and the mutual orientation of the surface under inspection, the illumination and a lens associated with the sensor is such that a specular reflection of light from diffuse source does not impinge directly on a lens associated with the sensor.

Additionally, focussed bright field illumination or focussed dark field illumination may be applied. Focussed bright field illumination refers to illumination in which the illumination is focussed to form a beam which is intersected by the surface under inspection, wherein orientation of the surface under inspection, the illumination and the sensor is such that a specular reflection of light from the focussed source impinges on a lens associated with the sensor. Focussed dark field illumination refers to illumination in which illumination is focussed to form a beam which is intersected by the surface under inspection, wherein orientation of the surface under inspection, the illumination and the sensor is such that a specular reflection of light from the focussed source does not impinge on a lens associated with the sensor.

It is appreciated that the surfaces of some articles inspected, for example FPDs, may include a periodic spatial feature that forms a diffraction grating. In the context of inspecting surfaces having such a periodic spatial feature, focussed dark field illumination is further categorized into on-axis and off-axis focussed dark field illumination. Focussed on axis dark field illumination refers to focussed dark field illumination in which the illumination source, the surface under inspection and the sensor are oriented such that the zero'th, or central, order of diffraction does not impinge on a lens associated with the sensor, however some other non-zero'th order of diffraction impinges on a lens associated with the sensor. Focussed off-axis dark field illumination refers to focussed dark field illumination in which the illumination source, the surface under inspection and the sensor are oriented such that no orders of diffraction impinge on a lens associated with the sensor, preferably because mutual axes along which diffraction orders converge are all outside the lens associated with the sensor.

Another aspect, of a preferred embodiment of the present invention relates to a system to inspect coatings applied to substantially flat surfaces of industrial objects, in which the coatings are applies, and subsequently inspected in using the apparatus and methods of the present invention.

There is thus provided in accordance with a preferred embodiment of the present invention a system for manufacture of flat panel displays including a plurality of manufacturing devices located in a first controlled environment, at least some of the plurality of manufacturing devices each including an enclosure defining a second controlled environment different from the first controlled environment, and a plurality of optical inspection devices operative to inspect flat panel display substrates at various stages of the production thereof by the plurality of manufacturing devices, at least some of the plurality of optical inspection devices being located within the enclosures defining the second controlled environments.

Preferably the first controlled environment is an airborne particle controlled environment having a first level of controlled airborne particulate contamination, and the second controlled environment is an airborne particle controlled environment having a second level of controlled airborne particulate contamination that is less than the first level of controlled airborne particulate contamination.

Further in accordance with a preferred embodiment of the present invention the plurality of optical inspection devices are operative in coordination with the plurality of manufacturing devices for inspecting the substrates prior to transfer thereof out of the second controlled airborne particle contamination environment.

Still further in accordance with a preferred embodiment of the present invention the at least some of the plurality of optical inspection devices include non-scanning sensors.

Additionally in accordance with a preferred embodiment of the present invention the plurality of optical inspection devices are operative to identify fabrication process defects occurring during production of flat panel display substrates.

Moreover in accordance with a preferred embodiment of the present invention the process defects include at least one of the following: uneven deposition of coatings, uneven removal of coatings, rinse residues, chemical residues, incomplete exposure of a photo-resist deposited on the substrate, cratches, lines, and particles embedded in the substrate.

Further in accordance with a preferred embodiment of the present invention the each of the plurality of optical inspection devices includes at least one non-scanning sensor which views substantially all of the surface of the substrate.

Still further in accordance with a preferred embodiment of the present invention the at least one non-scanning sensor includes a plurality of non-scanning sensors, each sensor viewing a portion of the substrate and together the plurality of sensors viewing substantially the entire surface of the substrate.

Additionally in accordance with a preferred embodiment of the present invention each of the plurality of optical inspection devices includes an illuminating array operative to provide various combinations of illumination.

Moreover in accordance with a preferred embodiment of the present invention the combinations include at least dark field and substantially bright field illumination.

Further in accordance with a preferred embodiment of the present invention the non-scanning sensor acquires at least one image of the substrate for each combination.

Still further in accordance with a preferred embodiment of the present invention the system also includes an image analyzer for identifying process defects by computer, analysis of a plurality of images of the substrate taken under various ones of the combinations of illumination.

Additionally in accordance with a preferred embodiment of the present invention, the image analyzer is operative without comparison to an external reference.

Moreover in accordance with a preferred embodiment of the present invention, the enclosure contains a first plurality of illuminators mounted on a first wall of the enclosure and a second plurality of illuminators mounted on a second wall of the enclosure, orthogonal to the first wall.

Further in accordance with a preferred embodiment of the present invention, the system also includes directionally adjustable illuminators.

Still further in accordance with another preferred embodiment of the present invention there is provided an inspection system for use in inspecting flat panel displays including a non-scanning optical array for viewing a flat panel display substrate, and an illumination subsystem sequentially providing dark field and bright field illumination of the flat panel display substrate when the optical array views the flat panel display substrate.

Additionally the illumination subsystem provides various combinations of dark field and bright field illumination of the flat panel display substrate when the optical array views the flat panel display substrate. The dark field and said bright field illumination may be diffuse or focussed.

Moreover, the flat panel display substrate may have a surface that includes a periodic spatial feature that is operative to diffract said dark field and said bright field illumination.

Further in accordance with a preferred embodiment of the present invention, the system includes a spatially positionable stage to support the flat panel display substrate, and the stage spatially positions the substrate at various angles relative to the illumination subsystem.

Still further in accordance with a preferred embodiment of the present invention, the optical array, illumination subsystem and stage are configured and arranged to selectively enable viewing the flat panel display substrate such that a non-zero'th order of diffraction impinges on the non-scanning optical array. Preferably, a multiplicity of the non-zero'th orders of diffraction of a similar order impinge on the non-scanning optical array.

Additionally, the optical array, the illumination subsystem and the stage are preferably configured and arranged to enable selectively viewing the flat panel display substrate such that a zero'th order of diffraction impinges on the non-scanning optical array.

Moreover, the optical array, the illumination subsystem and the stage are preferably additionally configured and arranged to enable selective viewing of the flat panel display substrate such that substantially no orders of diffraction impinge on the non-scanning optical array.

Preferably, the optical array, the stage and the illumination subsystem are configured and arranged to sequentially view the flat panel display substrate such that in one view a selected non-zero'th order of diffraction impinges on the optical array, and in other each sequential views at least one of the following orders of diffraction impinges on the optical array: a zero'th order of diffraction, an additional selected non-zero'th order of diffraction, no order of diffraction, the same non-zero'th order of diffraction of a different region of the article.

Additionally, in accordance with a preferred embodiment of the present invention the system also includes an image analyzer receiving an output from the non-scanning optical array and being operative to detect process defects including at least one of: uneven deposition of coatings, uneven removal of coatings, rinse residues, chemical residues, incomplete exposure of a photo-resist deposited on the substrate, scratches, lines, and particles embedded in the substrate.

Further in accordance with a preferred embodiment of the present invention the optical array views substantially all of a surface of the substrate. Alternatively, the optical array views only part of the surface of the substrate Still further in accordance with a preferred embodiment of the present invention the optical array acquires at least one image of the substrate for each of a plurality of different illuminations.

Additionally in accordance with a preferred embodiment of the present invention the image analyzer identifies the defects by computer analysis of a plurality of images of the substrate taken under differing illumination.

Moreover in accordance with a preferred embodiment of the present invention the system also includes an enclosure containing a first plurality of illuminators mounted on one wall thereof and a second plurality of illuminators mounted on a second wall thereof.

Further in accordance with a preferred embodiment of the present invention the system also includes a third illuminator mounted on a third wall of the enclosure.

Still further in accordance with a preferred embodiment of the present invention the system also includes a diffuser associated with the illumination subsystem.

Moreover in accordance with a preferred embodiment of the present invention the system includes a light source and a reflector operative to provide concentrated light from the light source to at least part of said flat panel display substrate.

Preferably, the reflector has two points of focus, and wherein a projector is situated at a first of points of focus, and the second point of focus is situated away from the flat panel display substrate. The reflector is preferably a section of an ellipsoid.

Alternatively, the reflector is flat and is operatively associated with a lens, which is preferably a fresnel lens attached to the reflector.

Moreover, in accordance with an additional alternative, the system includes light source, preferably a projector, and a lens operative to provide concentrated light from the light source to at least part of said flat panel display substrate. Preferably, the projector is situated at a first focus of the lens, and a second focus of the lens is situated away from the flat panel display substrate.

Additionally in accordance with a preferred embodiment of the present invention the system includes an adjustable mounting assembly for selectably determining at least one of relative inclination, spatial separation and axial orientation of at least two of the optical array, the illumination subsystem and the substrate.

There is also provided in accordance with a preferred embodiment of the present invention an inspection system for use in inspecting objects including a non-scanning optical array for viewing an object, and an illumination subsystem sequentially providing dark field and bright field illumination of the flat panel display substrate when the optical array views the object.

Further in accordance with a preferred embodiment of the present invention the illumination subsystem provides various combinations of dark field and bright field illumination of the object when the optical array views the surface.

Preferably, the dark field and said bright field illumination are diffuse or focussed.

Moreover, the surface may include a periodic spatial feature that operative to diffract light impinging thereon.

Additionally, the system preferably includes a spatially positionable stage to support the article, wherein the stage spatially positions the article at various angles relative to the illumination subsystem, and the optical array, illumination subsystem and stage are configured and arranged to selectively enable viewing the surface such that a non-zero'th order of diffraction impinges on the non-scanning optical array.

Additionally, the system is preferably arranged so that multiplicity of non-zero'th orders of diffraction of substantially the same order impinge on the non-scanning optical array. Preferably, the optical array, the illumination subsystem and the stage are configured and arranged such that the surface may be selectively viewed while a zero'th order of diffraction reflected from the surface impinges on the non-scanning optical array, or while no orders of diffraction impinge on the non-scanning optical array.

Preferably, the optical array the illumination subsystem and the stage are configured and arranged to sequentially view the article so that one view of the article a selected non-zero order of diffraction impinges on the optical array, and in other sequential views at least one of the following orders of diffraction impinges on the optical array: a zero'th order of diffraction, an additional non-zero'th order of diffraction, the same non-zero'th order of diffraction of a different region of the surface of the article, and no order of diffraction.

Still further in accordance with a preferred embodiment of the present invention the system also includes an image analyzer receiving an output from the non-scanning optical array and being operative to detect process defects including at least one of: uneven deposition of coatings, uneven removal of coatings, lines residues, chemical residues, incomplete exposure of a photo-resist deposited on the substrate, scratches, lines, particles.

Additionally in accordance with a preferred embodiment of the present invention the optical array views substantially all of a surface of the substrate. Alternatively, the optical array views only part of the surface of the substrate.

Moreover in accordance with a preferred embodiment of the present invention the optical array acquires at least one image of the substrate for each of a plurality of different illuminations.

Further in accordance with a preferred embodiment of the present invention the image analyzer identifies the defects by computer analysis of a plurality of images of the substrate taken under differing illumination.

Still further in accordance with a preferred embodiment of the present invention the system also includes an enclosure containing a first plurality of illuminators mounted on one wall thereof and a second plurality of illuminators mounted on a second wall thereof.

Additionally in accordance with a preferred embodiment of the present invention the system also includes a third illuminator mounted on a third wall of the enclosure.

Moreover in accordance with a preferred embodiment of the present invention the system also includes a diffuser associated with the illumination subsystem.

Additionally in accordance with a preferred embodiment of the present invention, the system includes a light source and a reflector operative to provide concentrated light from the light source to at least part of said surface. Preferably, the reflector has two points of focus. A projector preferably is situated at a first focus, and a second focus is situated not on the surface.

Further, in accordance with a preferred embodiment of the present invention, the reflector is a section of an ellipsoid. Alternatively, the reflector is flat and is operatively associated with a lens, which is preferably a fresnel lens attached to the reflector.

Alternatively, the system includes a light source, preferably a projector, and a lens operative to provide concentrated light from the light source to at leas; part of the flat panel display substrate. Preferably, the projector is situated at a first focus of the lens, and a second focus of the lens is situated not on the flat panel display substrate.

Further in accordance with a preferred embodiment of the present invention the system includes an adjustable mounting assembly for selectable determining at least one of relative inclination, spatial separation and axial orientation of at least two of the optical array, the illumination sub-system and the substrate.

There is also provided in accordance with a preferred embodiment of the present invention apparatus for optically inspecting the surface of an article having a substantially planar surface, including an inspection region, an illuminator operative to selectably illuminate the surface of an article located in the inspection region with at least two predetermined configurations of illumination, an image acquisition sub-system including at least one non-scanning camera for acquiring images of the surface of the article when illuminated by at least one predetermined configuration of illumination, and an image analysis subsystem for computer analyzing the images and detecting anomalies in the surface as a function of variations in reflected intensities of illumination. Based on the results of analysis of the surface, the article may be discarded, or subjected to further processing. Further processing may include correction of anomalies.

There is additionally provided a spatially positionable stage for supporting the article in the inspection region in selectable orientation relative to the illumination apparatus.

Moreover, in accordance with a preferred embodiment of the invention the image analysis subsystem is operative to identify anomalies that are substantially the same size as the resolution of the camera.

There is additionally provided in accordance with a preferred embodiment of the present invention apparatus for coating an article having a substantially planar surface, including a coating generator operative to generate a coating on a surface of the article, an illuminator for selectably illuminating the surface bearing the coating with at least two predetermined configurations of illumination, an image acquisition sub-system including at least one non-scanning sensor for acquiring images of the surface of the article for each combination of illumination, and an image analysis subsystem for analyzing the images and detecting anomalies in the surface on the basis of variations in reflected intensities of illumination.

There is also provided in accordance with a preferred embodiment of the present invention apparatus for inspecting an article in a clean room, including an inspection device situated in the clean room and including an inspection stage selectably positionable by remote control, at least one non-scanning sensor viewing the substantially the entire inspection stage, an array of illuminators illuminating the inspection stage, automated feed apparatus, a control station situated outside the clean room, the control station including a viewer for viewing articles placed in the inspection device and a controller for positioning the stage and providing selected configurations of illumination to illuminate the article.

There is also provided in accordance with a preferred embodiment of the present invention a method for manufacture of flat panel displays including providing a plurality of manufacturing devices located in a first controlled environment, at least some of the plurality of manufacturing devices each including an enclosure defining a second controlled environment different from the first controlled environment, and inspecting flat panel display substrates at various stages of the production thereof by the plurality of manufacturing devices at a location within the enclosures defining a second controlled environment.

Further in accordance with a preferred embodiment of the present invention the inspecting step includes inspecting the substrates prior to transfer thereof out of the second controlled airborne particle contamination environment.

Still further in accordance with a preferred embodiment of the present invention the inspecting step includes inspecting using non-scanning sensors.

Additionally in accordance with a preferred embodiment of the present invention the method further includes identifying fabrication process defects occurring during production of flat panel display substrates.

Moreover in accordance with a preferred embodiment of the present invention the identifying step includes identifying process defects including at least one of the following: uneven deposition of coatings, uneven removal of coatings, rinse residues, chemical residues, incomplete exposure of a photo-resist deposited on the substrate, scratches, lines, and particles embedded in the substrate.

Further in accordance with a preferred embodiment of the present invention the inspecting step includes inspecting using at least one non-scanning sensor which views substantially all of the surface of the substrate.

Still further in accordance with a preferred embodiment of the present invention the inspecting step includes inspecting using a plurality of non-scanning sensors, each sensor viewing a portion of the substrate and together the plurality of sensors viewing substantially the entire surface of the substrate.

Additionally in accordance with a preferred embodiment of the present invention the inspecting step includes illuminating the substrate with an illuminating array operative to provide various combinations of illumination.

Moreover in accordance with a preferred embodiment of the present invention the combinations include at least dark field and substantially bright field illumination.

Further in accordance with a preferred embodiment of the present invention the inspecting step includes acquiring at least one image of the substrate for each combination using the non-scanning sensor.

Still further in accordance with a preferred embodiment of the present invention the method also includes performing computer analysis of a plurality of images of the substrate taken under various ones of the combinations of illumination to detect process defects.

Additionally in accordance with a preferred embodiment of the present invention the image analysis step is performed without comparison to an external reference.

Moreover in accordance with a preferred embodiment of the present invention the providing step includes further mounting a first plurality of illuminators on a first wall of the enclosure and mounting a second plurality of illuminators on a second wall of the enclosure, orthogonal to the first wall.

Further in accordance with a preferred embodiment of the present invention the mounting step includes further providing directionally adjustable illuminators.

There is also provided in accordance with a preferred embodiment of the present invention a method for inspecting a flat panel display substrate including viewing a flat panel display substrate using a non-scanning optical array, and sequentially illuminating the flat panel display substrate with dark field and bright field illumination while the optical array views the flat panel display substrate.

Further in accordance with a preferred embodiment of the present invention the sequentially illuminating step illuminates using various combinations of dark field and bright field illumination of the flat panel display substrate when the optical array views the flat panel display substrate.

Still further in accordance with a preferred embodiment of the present invention the method also includes receiving an output from the non-scanning optical array, and detecting process defects including at least one of: uneven deposition of coatings, uneven removal of coatings, lines residues, chemical residues, incomplete exposure of a photo-resist deposited on the substrate, cratches, lines, and particles embedded in the substrate.

Additionally in accordance with a preferred embodiment of the present invention the viewing step includes viewing substantially all of a surface of said substrate.

Moreover in accordance with a preferred embodiment of the present invention the viewing step includes acquiring at least one image of the substrate for each of a plurality of different illuminations.

Further in accordance with a preferred embodiment of the present invention the detecting step includes identifying the defects by computer analysis of a plurality of images of the substrate taken under differing configurations of illumination.

Still further in accordance with a preferred embodiment of the present invention the method also includes providing an enclosure containing a first plurality of illuminators mounted on one wall thereof and a second plurality of illuminators mounted on a second wall thereof.

Additionally in accordance with a preferred embodiment of the present invention the providing step also includes providing a third illuminator mounted on a third wall of the enclosure.

Moreover in accordance with a preferred embodiment of the present invention the method also includes providing a diffuser associated with the illumination subsystem.

Further in accordance with a preferred embodiment of the present invention the method also includes providing an adjustable mounting assembly for selectably determining at least one of relative inclination, spatial separation and axial orientation of at least two of the optical array, the illumination subsystem and the substrate.

There is also provided in accordance with a preferred embodiment of the present invention a method for inspecting objects including viewing an object using a non-scanning optical array, and sequentially illuminating the object with dark field and bright field illumination while the optical array views the object.

Further in accordance with a preferred embodiment of the present invention the sequentially illuminating step illuminates using various combinations of dark field and bright field illumination of the object while the optical array views the object.

Still further in accordance with a preferred embodiment of the present invention the method also includes receiving an output from the non-scanning optical array, and detecting process defects including at least one of: uneven deposition of coatings, uneven removal of coatings, rinse residues, chemical residues, incomplete exposure of a photo-resist deposited on the substrate, cratches, lines, and particles embedded in the substrate.

Additionally in accordance with a preferred embodiment of the present invention the viewing step includes viewing substantially all of a surface of the object.

Moreover in accordance with a preferred embodiment of the present invention the viewing step includes acquiring at least one image of the object for each of a plurality of different illuminations.

Further in accordance with a preferred embodiment of the present invention the detecting step includes identifying the defects by computer analysis of a plurality of images of the object taken under differing configurations of illumination.

Still further in accordance with a preferred embodiment of the present invention the method also includes providing an enclosure containing a first plurality of illuminators mounted on one wall thereof and a second plurality of illuminators mounted on a second wall thereof.

Additionally in accordance with a preferred embodiment of the present invention the providing step also includes providing a third illuminator mounted on a third wall of the enclosure.

Moreover in accordance with a preferred embodiment of the present invention the method also includes providing a diffuser associated with the illumination subsystem.

Further in accordance with a preferred embodiment of the present invention the method also includes providing an adjustable mounting assembly for selectably determining at least one of relative inclination, spatial separation and rotational orientation of at least two of the optical array, the illumination subsystem and the object.

There is also provided in accordance with a preferred embodiment of the present invention a method for optically inspecting the surface of an article having a substantially planar surface, including defining an inspection region, selectably illuminating the surface of an article located in the inspection region with at least two predetermined configurations of illumination, for each predetermined configuration of illumination acquiring an image of the surface of the article using at least one non-scanning camera, and analyzing the image and detecting anomalies in the surface as a function of variations in reflected intensities of illumination.

There is additionally provided in accordance with a preferred embodiment of the present invention a method for coating an article having a substantially planar surface, including generating a coating on a surface of the article, selectably illuminating the surface bearing the coating with at least two predetermined configurations of illumination, for each configuration of illumination acquiring an image of the surface of the article using at least one non-scanning sensor, and analyzing the images and detecting anomalies in the surface on the basis of variations in reflected intensities.

There is also provided in accordance with a preferred embodiment of the present invention a method for inspecting an article in a clean room, including situating an inspection device in the clean room, selectably positioning an inspection stage of the inspection device by remote control, viewing substantially the entire inspection stage using at least one non-scanning sensor of the inspection device, illuminating the inspection stage using an array of illuminators of the inspection device, placing articles in the inspection device using automated feed apparatus of the inspection device, and situating a control station outside the clean room, the control station including a viewer for viewing articles placed in the inspection device and a controller for remotely positioning the stage and providing selected combinations of illumination.

There is additionally provided in accordance with a preferred embodiment of the present invention a method for inspecting the surface of an article, including the steps of placing the article in an inspection region defined by a stage, illuminating a portion of the surface of the article with at least one configuration of dark field illumination, acquiring an image of substantially the entire surface for the at least one configuration of dark field illumination, illuminating the surface with at least one configuration of substantially bright field illumination, acquiring an image of substantially the entire surface for the at least one configuration of substantially bright field illumination, and providing computer analysis of the images to determine non uniformities in reflected intensities.

Further in accordance with a preferred embodiment of the present invention the at least one configuration of dark field illumination includes a plurality of dark field illumination configurations, and a separate image is acquired for each configuration.

Still further in accordance with a preferred embodiment of the present invention the at least one configuration of substantially bright illumination includes a plurality of bright field illumination configurations, and a separate image is acquired for each configuration.

Additionally in accordance with a preferred embodiment of the present invention each predetermined combination of illumination is provided by selecting a predetermined inclination and rotational orientation of the substrate, and separate images of the surface are acquired for each inclination and rotational orientation.

Moreover in accordance with a preferred embodiment of the present invention there is provided an additional step of optically treating the illumination prior to acquiring an image.

Further in accordance with a preferred embodiment of the present invention the treatment is provided by optical filters.

Still further in accordance with a preferred embodiment of the present invention the filters filter for selected wavelengths.

Additionally in accordance with a preferred embodiment of the present invention the filters filter for selected polarization.

Moreover in accordance with a preferred embodiment of the present invention the surface is illuminated with a selected combination of broad spectrum illumination and imaged through an optical filter operative to transmit light in a first predetermined spectral range, and subsequently imaged through and optical filter operative to transmit light in a second predetermined spectral range.

Further in accordance with a preferred embodiment of the present invention the surface is illuminated with a first combination of illumination through an optical filter operative to transmit light predetermined spectral range and imaged, and subsequently illuminated with a second combination of illumination through an optical filter operative to transmit light in a second predetermined spectral range and imaged.

Still further in accordance with a preferred embodiment of the present invention the surface is illuminated with a selected combination of broad spectrum illumination and imaged through and optical filter operative to transmit light having a first polarization state, and subsequently imaged with through a second optical filter operative to transmit light having a second predetermined polarization state.

Additionally in accordance with a preferred embodiment of the present invention the surface is illuminated with a first combination of optically filtered illumination having a first predetermined polarization state and imaged, and subsequently illuminated with a second combination of optically filtered illumination having a second predetermined polarization state and imaged.

Moreover in accordance with a preferred embodiment of the present invention there is provided an additional step of blurring the image during acquisition.

Further in accordance with a preferred embodiment of the present invention an image is blurred by introducing, during image acquisition, relative movement between at least two of the following: the surface, the camera, and an optical element between the surface and the camera.

Still further in accordance with a preferred embodiment of the present invention there is provided a further step of analyzing the non-uniformities in reflective intensity with a computer to determine the presence of defects in coatings on the substrate.

Additionally in accordance with a preferred embodiment of the present invention the article is a flat display panel substrate.

There is also provided in accordance with a preferred embodiment of the present invention a method for coating the surface of an article, including the steps of depositing a coating on at least part of a surface of the article, placing the article in an inspection region, illuminating a portion of the coated surface of the article with dark field illumination and acquiring an image of the illuminated surface, illuminating the surface with substantially bright field illumination and acquiring an image of the illuminated surface, and analyzing each image with a computer to determine non uniformities in reflected intensity.

There is also provided in accordance with a preferred embodiment of the present invention apparatus for the automatic optical inspection of a generally flat article having at least one generally periodic spatial feature, comprising a light beam generator providing an illuminating beam of light along an illuminating light beam axis onto a generally flat article having at least one at least generally periodic spatial feature; and a sensor viewing the article along a light receiving axis disposed at an angle with respect to the illumination light beam axis whereby a generally non-zero'th order of diffracted light reflected from the said article impinges on the sensor.

Further in accordance with a preferred embodiment of the present invention, there is provided a selectably orientable support supporting the generally flat article, and a postioner for changing the angular inclination of the generally flat article with respect to the illumination light beam axis and said light receiving axis during viewing by the sensor.

Preferably, the positioner is operative to selectably orient the generally flat article so that it lies in a plane that is not always perpendicular to the plane defined by the illuminating light beam axis and the light receiving axis.

Still further in accordance with a preferred embodiment of the present invention, there is provided a light absorbing housing enclosing at least said light beam generator and the sensor for generally preventing diffuse illumination from impinging on said sensor is also provided.

There is also provided in accordance with a preferred embodiment of the present invention a method for manufacturing flat panel displays including the steps of providing a first controlled environment in which an airborne particle controlled environment having a first level of controlled airborne particulate contamination, and a second controlled environment in which an airborne particle controlled environment having a second level of controlled airborne particulate contamination is less than the first level of controlled airborne particulate contamination.

Further in accordance with a preferred embodiment of the present invention the method of inspecting a flat panel display includes illuminating the dark field and the bright field illumination are diffuse. Prefrably, the dark field and the bright field illumination are focussed.

Additionally in accordance with a preferred embodiment of the present invention the flat panel displays substrate has a surface that includes a periodic spatial feature, and the dark field and the bright field illumination are diffracted by the spatial feature.

Still further in accordance with a preferred the optical array, illumination subsystem and stage are configured and arranged to selectively enable viewing the flat panel display substrate such that a non-zero'th order of diffraction impinges on the non-scanning optical array. Additionally a multiplicity of the non-zero'th orders of diffraction of a similar order impinge on said non-scanning optical array.

Still further in accordance with a preferred embodiment of the present invention, the method for inspecting the flat panel display includes configuring and arranging the optical array, the illumination subsystem and the stage to additionally enable selectively viewing the flat panel display substrate such that a zero'th order of diffraction impinges on the non-scanning optical array. Additionally, the optical array, the illumination subsystem and the stage are configured and arranged to additionally enable selective viewing of the flat panel display substrate such that substantially no orders of diffraction impinge on the non-scanning optical array.

Furthermore, the optical array and the illumination subsystem are configured and arranged to sequentially view the flat panel display substrate and wherein in one view a selected non-zero'th order of diffraction impinges on the optical array, and in other each sequential views at least one of the following impinges on the optical array: a zero'th order of diffraction, an additional selected non-zero'th order of diffraction, no order of diffraction, the same non-zero'th order of diffraction of a different region of the article.

The method for inspecting a flat panel display includes providing a light source and a reflector operative to provide concentrated light from the light source to at least part of said flat panel display substrate. Additionally the reflector has two points of focus, and wherein a projector is situated at a first of points of focus, and the second point of focus is situated away from the flat panel display substrate. The reflector may be a section of an ellipsoid. Alternatively, the reflector may be flat and operatively associated with a lens, and the lens may include a fresnel lens attached to the reflector.

Furthermore the method for inspecting a flat display panel may include providing a light source and a lens operative to provide concentrated light from the light source to at least part of the flat panel display substrate. Additionally the projector is situated at a first focus of the lens, and a second focus of the lens is situated away from the flat panel display substrate.

In a method for inspecting a flat display panel the dark field and the bright field illumination may be diffuse. Additionally, the dark field and the bright field illumination may be focussed, and the surface includes a periodic spatial feature operative to diffract light impinging, thereon.

The method also includes providing a spatially positionable stage to support the article, wherein the stage spatially positions the article at various angles relative to the illumination subsystem. Additionally, the optical array, illumination subsystem and stage are configured and arranged to selectively enable viewing the surface such that a non-zero'th order of diffraction impinges on the non-scanning optical array, and the multiplicity of non-zero'th orders of diffraction of substantially the same order impinge on the non-scanning optical array. Furthermore, the optical array, the illumination subsystem and the stage are configured and arranged to additionally enable selectively viewing of the surface such that a zero'th order of diffraction impinges on the non-scanning optical array. Furthermore, the optical array, the illumination subsystem and the stage are configured and arranged to additionally enable selectively viewing the object such that substantially no orders of diffraction impinge on the non-scanning optical array. The optical array, the illumination subsystem and the stage are also configured and arranged to sequentially view the object and wherein in one view a selected non-zero order of diffraction impinges on the optical array, and in other sequential views at least one of the following impinges on the optical array: a zero'th order of diffraction, an additional non-zero'th order of diffraction, the same non-zero'th order of diffraction of a different region of the surface of the article, and no order of diffraction.

Additionally the optical array views only a part of a surface of the substrate.

The method for inspecting a flat panel display also includes providing a light source and a reflector operative to provide concentrated light from the light source to at least part of said surface wherein the reflector has two points of focus, and wherein a projector is situated at a first focus, and a second focus is situated not on the surface.

The reflector is a section of an ellipsoid or alternatively the reflector may be flat and is operatively associated with a lens. The lens may be a fresnel lens attached to the reflector.

The method for inspecting a flat panel display also includes providing a light source and a lens operative to provide concentrated light from the light source to at least part of the flat panel display substrate, and a projector which is situated at a first focus of the lens, and a second focus of the lens is situated not on the flat panel display substrate.

BRIEF DESCRIPTION OF THE DRAWINGS

The present invention will be more fully appreciated from the following detailed description taken in conjunction with the accompanying drawings, in which:

FIG. 1 is a simplified pictorial illustration of a clean room for FPD fabrication having located therein a system for inspecting FPD substrates constructed and operative according to a preferred embodiment of the present invention;

FIG. 14 is a simplified pictorial illustration of an illumination and image acquisition subsystem configured and arranged in a accordance with a preferred embodiment of the present invention to provide focussed bright field and focussed dark field illumination showing axes of inclination and rotation of a stage therein;

FIGS. 15A-15E are simplified side view illustrations of an illumination and acquisition subsystem constructed and arranged in accordance with a preferred embodiment of the present invention showing the effect of changing the angle of inclination of a stage;

FIGS. 16A and 16B are simplified pictorial illustrations of an illumination and image acquisition subsystem constructed and arranged in accordance with a preferred embodiment of the present invention showing on-axis focussed dark-field and off-axis focussed dark field illumination, respectively;

FIGS. 17A and 17B are simplified side view illustrations of an illumination and image acquisition system constructed and arranged in accordance with a preferred embodiment of the present invention illustrating diffraction when focussed and diffuse illumination are provided.

FIG. 20 is a simplified pictorial illustration of an additional preferred embodiment of an inspection system constructed and operative in accordance with the present invention.

DETAILED DESCRIPTION OF PREFERRED EMBODIMENTS

Figure 2A:
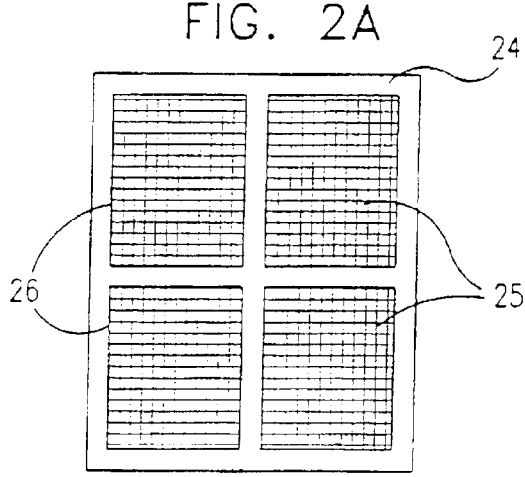
FIGS. 2A-2E are simplified illustrations of a typical FPD substrate and various typical fabrication process flaws which may occur during fabrication thereof.
Figure 2B:
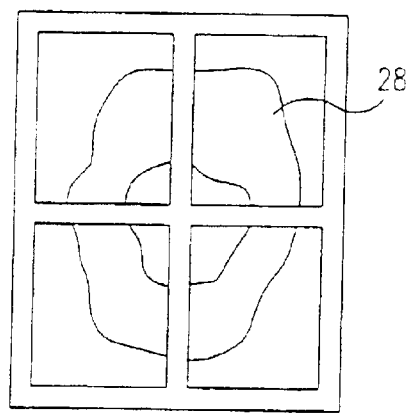
Figure 2C:
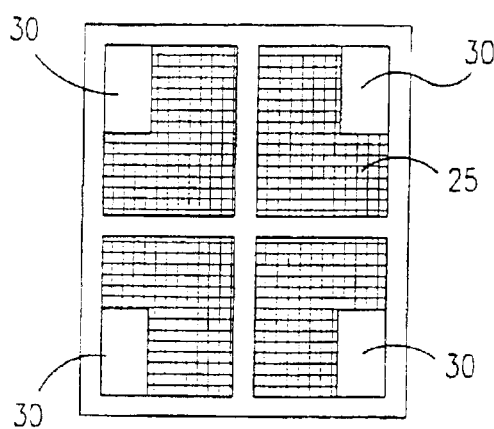
Figure 2D:
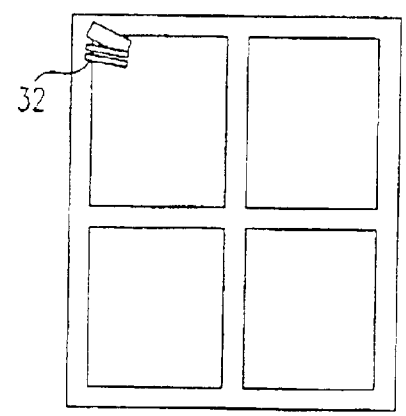

Reference is made to FIG. 1, which illustrates part of an FPD fabrication facility 10 comprising a number of units of fabrication equipment 12, at least some of which include an inspection system 14 constructed and operative in accordance with the present invention.

FPD fabrication is extremely sensitive to contamination by airborne particles. FPD fabrication is therefore conducted in so-called "clean areas", having a controlled environment of highly filtered air. Various processes require different tolerances of air purity. A typical clean area used for FPD fabrication, such as a clean room, may have a concentration of airborne particulate impurities, such as dust, of between 10–100 particles per cubic meter of air. In order to maintain such low concentrations of airborne particles, FPD fabrication operations are preferably highly mechanized and run without human intervention.

Fabrication equipment 12 is generally highly automated and self-contained. Each unit of equipment 12 is situated in a clean room 15 and performs a predetermined series of fabrication process steps. Automated trolleys 16 running on pathways 18 in the clean room are used to transport cassettes 20 of in-fabrication FPD substrates to and from the automated fabrication equipment 12 during the fabrication process. To minimize contamination, only a few human attendants 22 are permitted into the clean room 15. Moreover, attendants 22 in the clean room 15 are required to wear specialty designed attire to further reduce contamination.

FPD structures and fabrication processes are well known and are described in detail, for example in Castellano. J. et. Al., "Liquid Crystal Displax's ", Stanford Resources, Inc., 1995. The particulars of any given fabrication process are not part of this invention. A generalized description of FPD structure and fabrication, is now provided by way of example only in order that the description of the present invention may be more readily understood.

A typical FPD substrate, shown in FIG. 2A, comprises a glass substrate 24 having a multi-layered matrix structure, typically comprising a periodic spatial array of features, such as individually controllable liquid crystal cells 25, uniformly deposited thereon. The size of each cell is typically in the order of 90×270 microns. The cells 25 are interconnected by connectors (not shown) having a typical line width of the order of 7 microns. A typical substrate measures between 405×505 mm and 650×830 mm and contains a plurality of multi-layered matrices 26, of which four are shown. It is readily appreciated that a dense structure of cells and connectors typically forms a two dimensional diffraction grating when appropriately illuminated.

The matrix structure is preferably obtained by a repetitive multi-step process generally including the deposition of a metallic or non-metallic thin film on the substrate 24; coating the film with a radiation sensitive photoresist; exposing the photoresist to radiation according to a predetermined pattern; developing the photoresist and selectively washing away those parts of the photoresist that are exposed (or in some processes, not exposed); etching away those parts of the thin film not protected by residual photoresist, to thereby form the predetermined pattern in the thin film; and stripping away residual photoresist that overlays the resulting pattern. Each of these steps may be performed by various alternative techniques, the particulars of which are not of importance for the current invention. As the result of multiple repetitions of the foregoing steps, multi-layered matrices 26 are generated.

Typically each unit of fabrication equipment 12 handles a number of associated steps in the fabrication process. For example, some fabrication equipment deposits thin metallic film layers on the glass substrate 24. Other fabrication equipment coats the resulting metallic film with photoresist, exposes the photoresist according to a pattern, develops the photoresist and selectively removes exposed or unexposed photoresist. Still other fabrication equipment etches the metallic layer to remove those parts of the metal film that are not protected by residual photoresist. Still further fabrication equipment strips residual photoresist overlying the resultant pattern.

A typical clean room comprises an area of hundreds of square meters. Because human attendants cannot be excluded from such clean rooms and because of the extremely high cost of maintaining clean rooms at the lower end of the permitted range of contamination, the large clean rooms typically have a concentration level of airborne particles per cubic meter that is maintained at the upper end of the permitted range, approximately 100 airborne particles per cubic meter.

In order to meet the environmental demands required by some of the fabrication steps within the clean room 15, for example low airborne particulate concentration, various critical units of fabrication equipment 12 are each provided with an enclosure defining a second controlled self-contained environment that meets the required environmental demands. This second self-contained environment is typically maintained at a lower level of airborne contamination than that of the clean room 15. For typical fabrication equipment, the self-contained environment is maintained preferably at about 10 airborne particles per cubic meter.

Inside the second self-contained controlled environment, in-fabrication FPD substrates are typically handled by robots (not shown). FPDs are typically fabricated in batches, with each batch being carried in cassettes 20 between various second self-contained environments situated at different locations in the clean room.

Figure 2E:
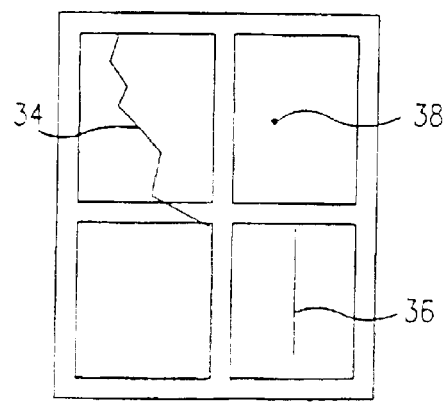

Processes that are performed in fabrication equipment 12 are potentially subject to process flaws. Referring now to FIGS. 2-2E, illustrative examples of typical detectable large scale process flaws are shown. Typical fabrication process flaws include; deposits of chemical residues 28 that remain on the substrate because of incomplete washing (FIG. 2B); areas 30 of incomplete or missing matrix resulting from uneven exposure of photoresist, and subsequent uneven or incomplete deposition of matrix 26 in those areas (FIG. 2C); rinse tracks 32 that remain on the substrate after washing between processes (FIG. 2D); scratches 34, lines 36 and embedded particles 38 (FIG. 2E). Additional fabrication process defects include various other anomalies such as uneven deposition of films and coatings on the substrate (not shown). It is to be appreciated that this list of fabrication process flaws may be considered representative of typical defects, and is not limiting.

Process flaws such as those described above may affect individual FPD substrates, or an entire batch of FPD substrates being processed by a particular unit of fabrication equipment. For example, a robot loader that handles FPD substrates inside fabrication equipment 12 may scratch all the substrates that it handles, thus rendering the substrates defective, or the timing of a rinse may be improperly set so that chemical residues are not fully washed off the substrate.

In order to identify defective in-fabrication FPD substrates as early as possible in the fabrication process, in accordance with a preferred embodiment of the present invention, optical inspection apparatus 14 is situated inside the controlled self-contained environment of fabrication equipment 12 to automatically inspect substrates 24 after the completion of a fabrication process but before removal to fabrication equipment performing downstream fabrication processes. In accordance with an additional feature of the present invention, optical inspection apparatus 14 constructed and operative in accordance with the present invention may be configured as stand-alone equipment situated in the clean room, but outside of equipment 12.

Figure 3:
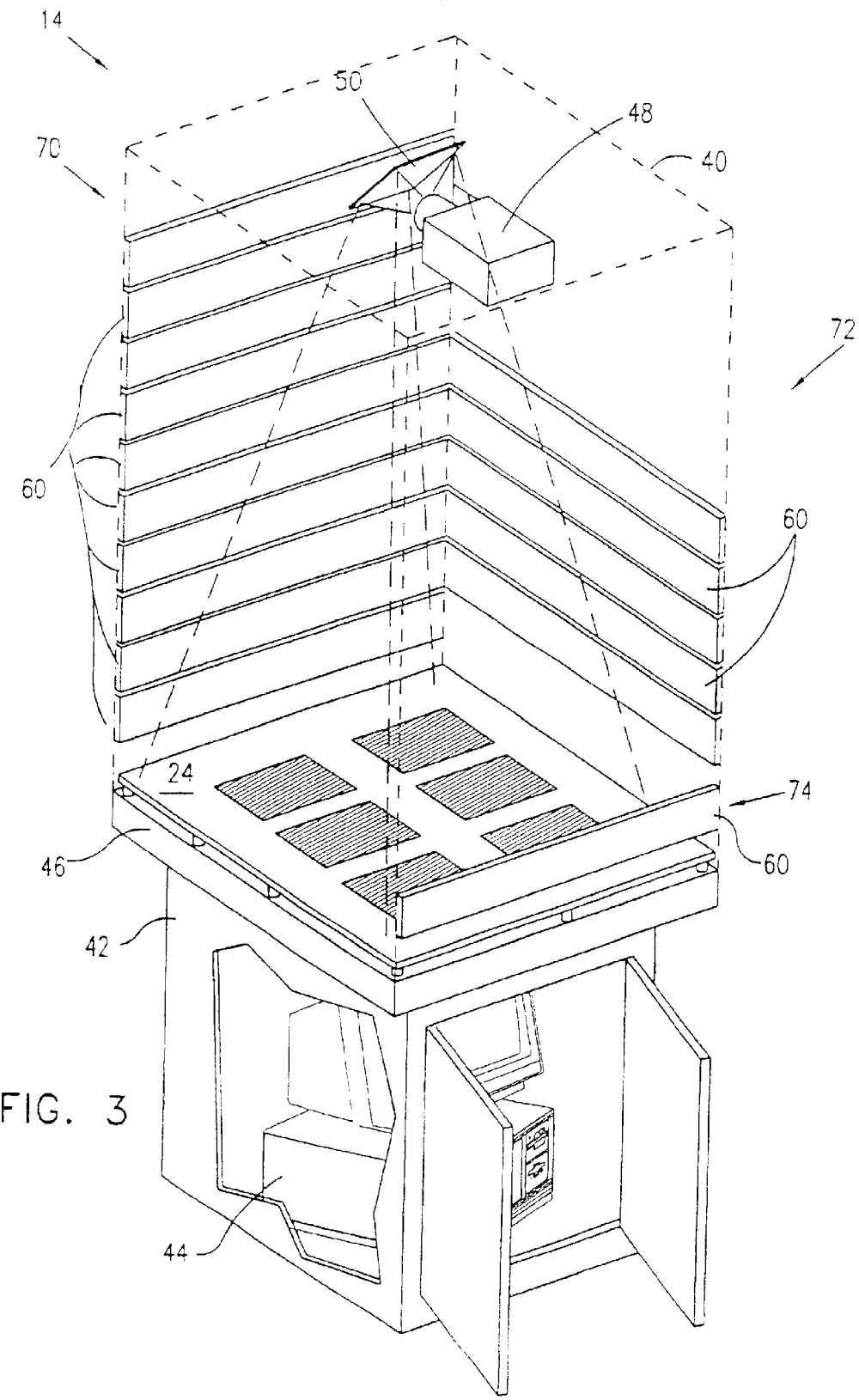
FIG. 3 is a simplified pictorial illustration of an inspection system constructed and operative in accordance with a preferred embodiment of the present invention.

Reference is made to FIG. 3, which is a perspective view of inspection apparatus 14, constructed and operative in accordance with a preferred embodiment of the invention operative to provide multiple arrangements of diffuse lighting, and to identify, defective FPD substrates. Inspection apparatus 14 preferably comprises an upper substantially fully enclosed inspection enclosure 40 shown in phantom lines, and a lower computer cabinet 42 in which a computer controller and image processor 44, preferably an Ultra Sparc AXI 300, available from Sun Micro Systems Corp., is situated. The width and depth dimensions of inspection enclosure 40 are preferably up to about 1.2 m width, by 1.0 m depth, these dimensions being somewhat larger than the dimensions of typical FPD substrates. It is readily appreciated that larger and smaller dimensions may be used in order to accommodate larger and smaller substrates. The height of enclosure 40 is preferably 1.00–1.30 meters in height, depending on the desired inspection resolution and dimensional constraints of the fabrication equipment 12 in which it is situated. Optionally the entire inspection apparatus 14 may be tilted to one side in order to accommodate space constraints imposed by fabrication equipment 12.

A stage 46 is situated in the base of inspection enclosure 40 for supporting an in-fabrication FPD substrate 24. A non-scanning staring array sensor 48, preferably a CCD type non-scanning staring area camera having between 1,200×1,000 and 1,500×1,000 pixel resolution, s secured to enclosure 40 overhead of stage 46. Sensor 48 is preferably a Hammamatsu C4742-95 CCD camera, provided with a wide angle lens, preferably a Nikkor AF 20 mm lens from Nikon Corporation. As is readily appreciated, the camera and lens arrangement provide a field of view that is sufficient to view at least a substantial part of the substrate 24, and preferably the entire substrate. As will be discussed in detail below with reference to FIG. 11, alternatively: an array of non-scanning sensors that together image the entire substrate, may be provided. Alternatively, sensor 48 may be arranged to view only a part of substrate 24, and substrate 24 may be sequentially rotated.

In accordance with a preferred embodiment of the present invention, the sensor 48 is horizontally mounted on top of enclosure 40, and is provided with a flat angularly adjustable reflector 50, configured to direct an image of substrate 24 into sensor 48. It is readily appreciated that due to dimensional constraints on the height of enclosure 40 imposed by dimensional limitations of fabrication equipment 12 in which it is situated, it may be advantageous to locate sensor 48 elsewhere in the enclosure and to use mirrors (not shown) to fold the optical path. For example, an upward staring sensor positioned adjacent to the stage may be used in combination with a substantially downward reflecting mirror to effectively increase the optical distance between the sensor and the stage without having to increase the height of enclosure 40.

The walls of enclosure 40 are preferably constructed of metal, such as aluminum, and are provided with a light absorbing coating, such as a black matte coating, operative to minimize internal reflections inside enclosure 40. A small access opening (not shown) is provided so that fabrication substrates 24 can be readily positioned on stage 46, or removed therefrom.

Figure 4:
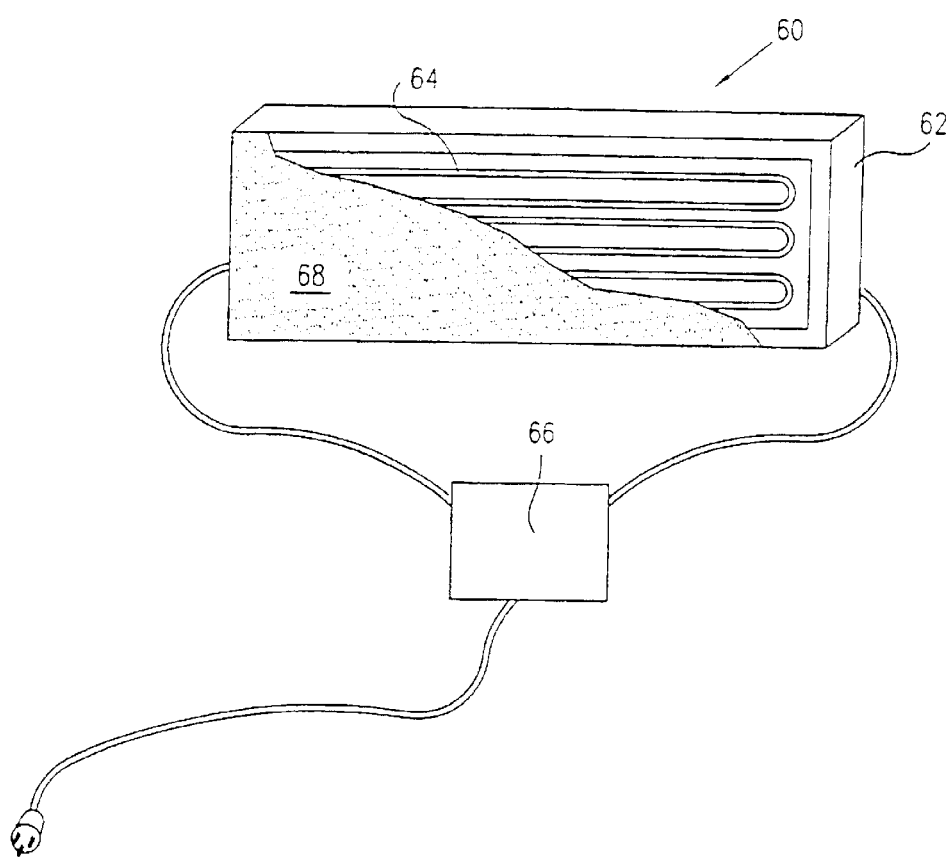
FIG. 4 is a simplified pictorial illustration of an illumination unit useful in a preferred embodiment of the invention.

An array of illumination units 60 is provided inside enclosure 40, for providing various selectable combinations of illumination, as will be explained in greater detail below. In accordance with a preferred embodiment of the present invention, each illumination unit 60, shown in detail in FIG. 4, preferably comprises a housing 62, a cold cathode lamp 64 located inside the housing, a power supply 66 and a diffuser 68. It is readily appreciated that instead of employing a wide visible spectrum cold cathode lamps, illumination units 60 may employ arrays of individually controllable LEDs configured to provide selectable combinations of wide spectrum or narrow spectrum illumination, flash units, or non-visible spectrum irradiators such as those providing illumination in the near UV spectral region. The diffuser 68 may be formed of a ground glass diffusing element, Fresnel diffuser or suitable diffusing elements.

As shown in FIG. 3, one wall of the inspection enclosure is preferably provided with a first illumination array, referred to herein as tall wall illumination array 70, beginning about 1 cm above stage 46, ranging between 1.00 meter to 1.30 meters in height above the stage 46, and covering substantially the entire width of an inside wall of the cabinet 42. Tall wall illumination array 70 is preferably divided into at least 10 individually controllable illumination units 60. A second illumination array, between 35–70 cm in height, referred to herein as short wall illumination array 72, is preferably provided on an inside wall of the enclosure 40, and is typically orthogonal to tall wall illumination array 70.

Short wall illumination array 72 preferably covers substantially the entire width of an inside wall of enclosure 40, preferably beginning at between 8 to 15 cm above the stage, and preferably comprises at least five individually controllable illumination units 60. A third illumination array, referred to as strip illumination array 74, preferably comprises a single independently controllable illumination unit 60. Strip illumination 74 preferably is situated on an inside wall of enclosure 40 preferably opposite tall wall illumination array 70, at height of between 5–10 cm above the stage 46.

Figure 5:
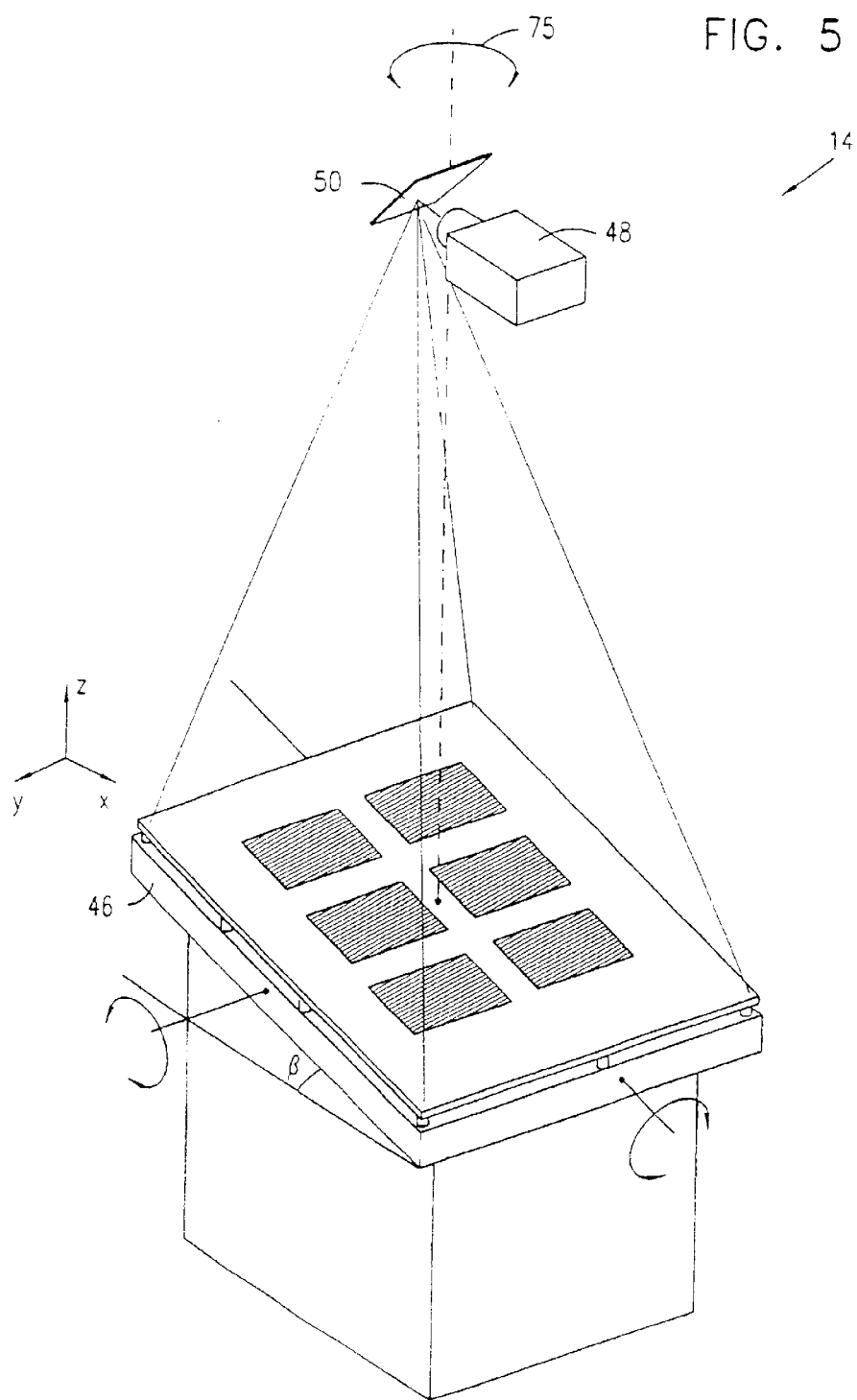
FIG. 5 is a simplified pictorial illustration of an inspection system having a stage which is movable about multiple axes in accordance with a preferred embodiment of the invention.

Referring now to FIG. 5, it is seen that the spatial orientation of stage 46 is adjustable. Horizontal inclination of stage 46 is preferably selectively adjustable to be at an angle $\beta$ relative to the horizontal in either the X–Z plane, as shown, or to the Y–Z plane. Inclination of stage 46 malt be selected using a linear positioning table, preferably a model 404XR table available from Daedal. Rotational positioning of stage 46 relative to its central axis 75 also may be adjusted using a conventional rotational positioning table (not shown).

One advantage of providing an array of separately controllable illumination elements 60 for illuminating the stage from different angles in combination with a spatially positionable stage 46 is that the angles of illumination between respective illumination units 60 and the stage 46 and between the stage and sensor 48 may thus be selected both to maximize the contrast of various process flaws associated with matrix 25 or substrate 24, and to minimize optical noise, such as the reflection of an image of sensor 48 back through its lens. For example, some process flaws may be better viewed when illuminated by substantially bright field illumination. Other types of process flaws may have higher contrast, and thus be better viewed, when illuminated by dark field illumination that is provided at selected angles to the substrate. It is readily appreciated that in providing a large selection of illumination combinations and of spatial positioning of the stage, typically including multiple combinations of dark field illumination and optionally, in addition, substantially bright field illumination, the contrast of different flaws can be maximized and noise minimized so as to enhance the ease of viewing different types of process flaws in at least one of the illumination configurations.

The operation of a preferred embodiment of the invention for various combinations of illumination and spatial positioning of the substrate 24, are now described with reference to FIGS. 6-8.

Figure 6:
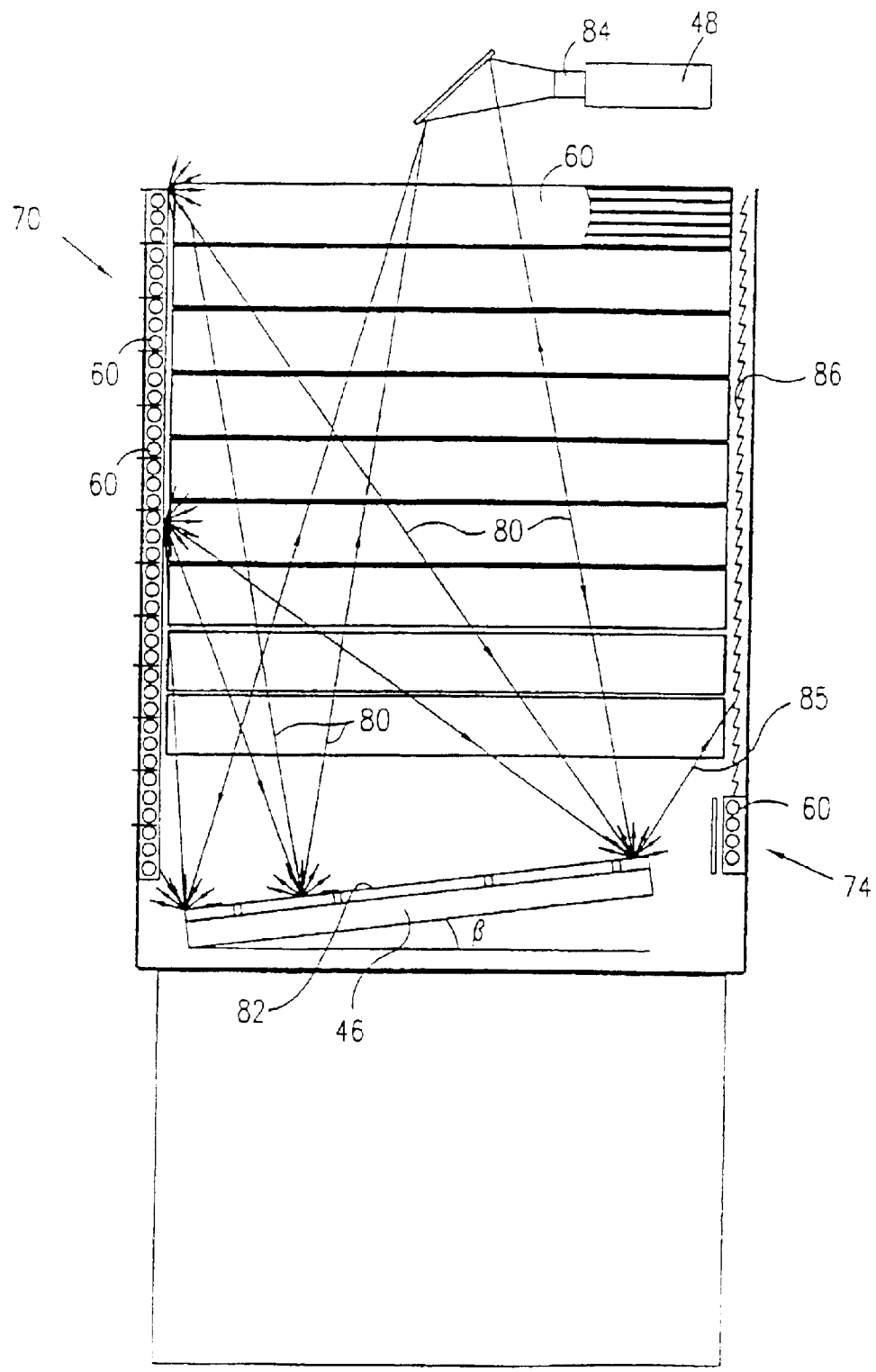
FIG. 6 is a simplified side view illustration of the geometry of diffuse bright field illumination employed in a preferred embodiment of the intention.

In a first illumination configuration, shown in FIG. 6, a flood diffuse illumination is provided. Here it is seen that rays 80, geometrically representing a bright field component of illumination, are reflected by a surface 82 of substrate 24 such that for a specularly reflecting surface at least some of rays 80 follow a path that impinges on lens 84 associated with sensor 48. It is appreciated that while this configuration of illumination is referred to herein as substantially bright field, the illumination is diffuse and for a clean and properly fabricated FPD substrate 24 (FIG. 3), the matrix structure 26 (FIG. 2) deposited on the substrate 24 at least partially diffracts and scatters the diffuse light, such that at least some of the rays, typified by non-bright field ray 85, do not impinge on lens 84. Consequently, patterns are typically formed in the reflection as result of non specular reflection corresponding to light diffracted and scattered by the pattern deposited on the substrate.

In order to achieve diffuse substantially bright field illumination, stage 46 is inclined toward the tall wall illumination array 70, preferably at an angle $\beta$ of between 18°–26° so that bright field components of rays 80 specularly reflected from all regions surface 82 impinge on lens 84. Preferably all of illumination units 60 of the tall wall illumination array 70 are illuminated simultaneously. Surface 82 is imaged by sensor 48, and the acquired image is subsequently processed by computer controller and image processor 44 (FIG. 3).

It is appreciated that in the diffuse substantially bright field configuration described, because of the diffuse illumination, each individual point on the stage may be considered as being illuminated by numerous point sources originating in tall wall illumination array 70, and that each individual point source in tall wall illumination 70 may be considered as illuminating numerous points on the surface 82. The result is an intense flood of diffuse multi-source illumination on surface 82.

It is also appreciated that while it is convenient to refer to such illumination as "bright field illumination", because a specularly reflected light from an illumination source, such as tall wall illumination 70, impinges on lens 84, in fact some of the illumination does not impinge on lens 84. The non-bright field components of the illumination can be generally considered "wasted" light. Preferably, internal walls of enclosure 40 are provided with a conventional anti-reflection coating 86 to minimize undesired reflections from non-bright field rays 85.

Figure 7:
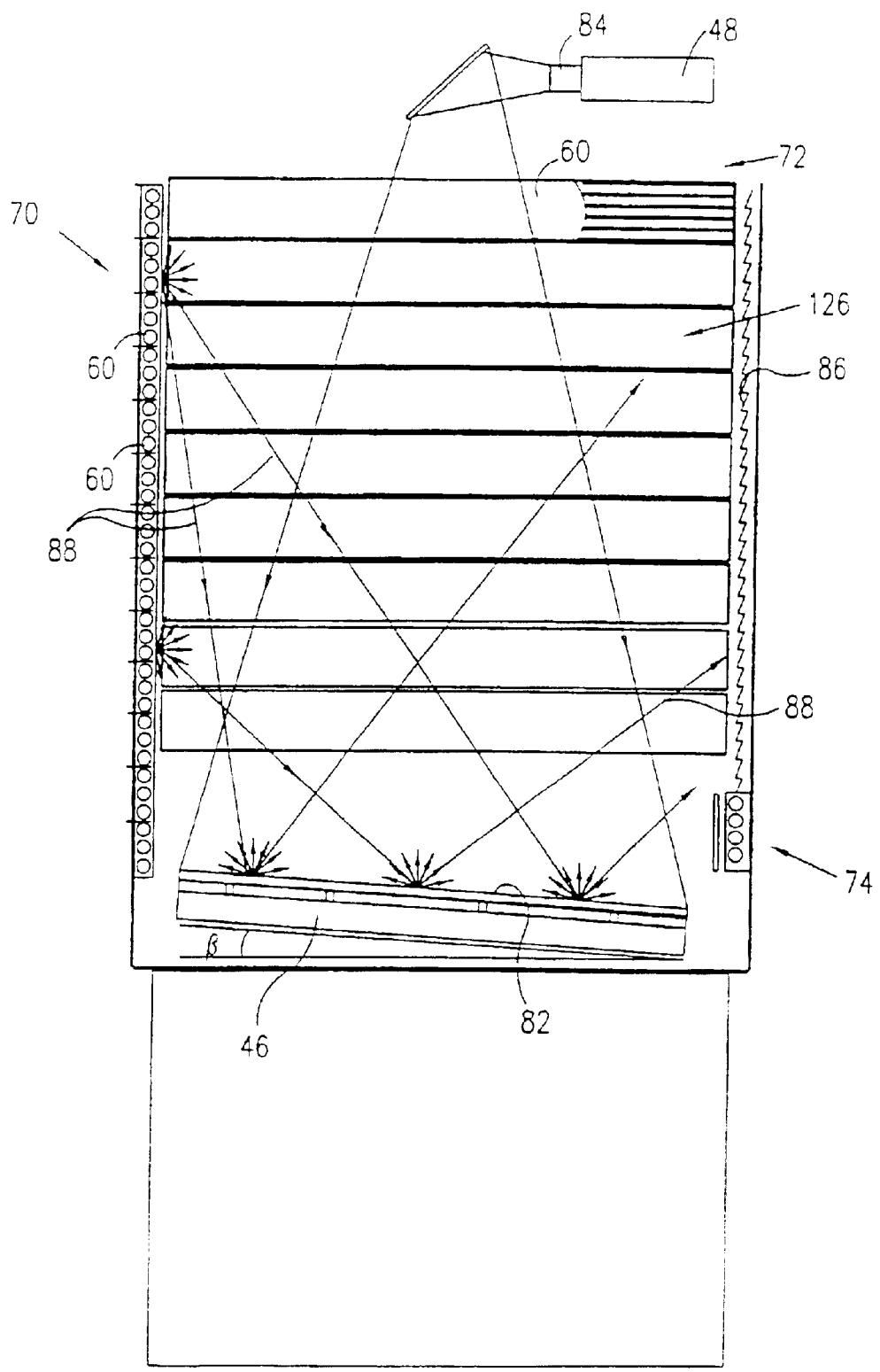
FIG. 7 is a simplified side view illustration of the geometry of one type of diffuse dark field illumination employed in a preferred embodiment of the invention.
Figure 8:
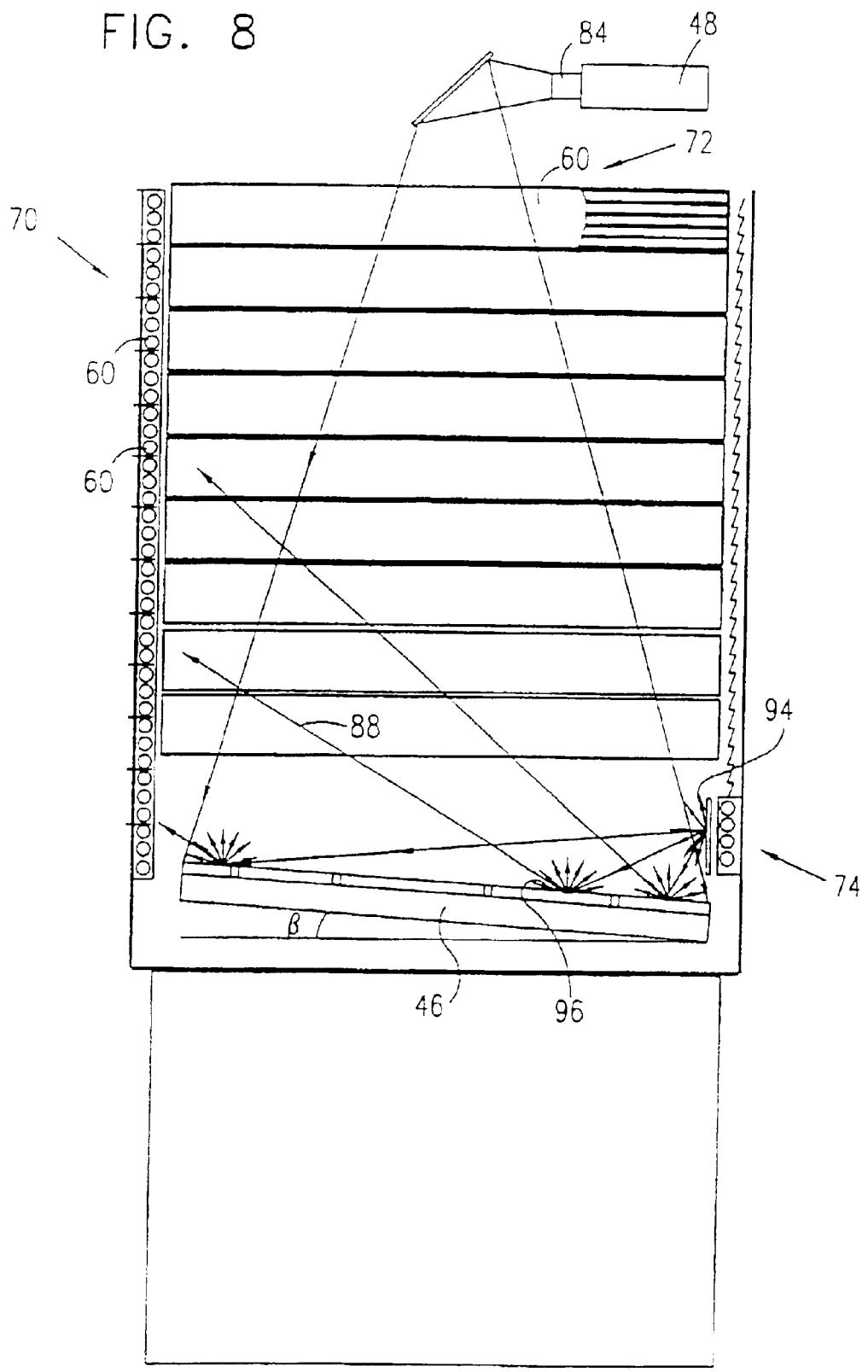
FIG. 8 is a simplified side view illustration of the geometry of another form of diffuse dark field illumination employed in a preferred embodiment of the invention.

Additional illumination configurations, shown in FIGS. 7 and 8, provide diffuse dark field illumination. As seen in FIGS. 7 and 8 none of rays 88, geometrically representing a component in the illumination that is reflected by a specularly reflecting surface 82 of substrate 24, impinge on lens 84 associated with sensor 48.

In a first diffuse dark field illumination configuration, shown in FIG. 7 stage 46 is inclined away from tall wall illumination array 70, preferably at an angle β, ranging between 12°–18° to the horizontal, so that an image of sensor 48 and all rays 88 from tall wall illumination array 70 are not specularly reflected by surface 82 back into lens 84. Initially, illumination is provided by predetermined combinations of illumination units 60 forming pan of tall wall illumination array 70. The units 60 in tall wall illumination array 70 that are employed for this purpose are preferably located between 5 and 50 cm above stage 46. The inclination of stage 46 and the angle of the illumination are selected to provide diffuse dark field illumination of at least part of surface 82. The surface 82 is imaged by sensor 48 for each of a plurality of different illumination configurations. If a given illumination configuration does not provide suitable diffuse dark field illumination of the entire surface 82, stage 46 may be rotated as necessary. Preferably, a second combination of dark field illumination is provided in which the units 60 that are located in the range of 40–90 cm above stage 46 are employed to illuminate at least part of surface 82.

In a similar manner, diffuse dark field illumination preferably is additionally provided by illumination units 60 forming part of short wall illumination array 72.

Referring now to FIG. 8, there is seen a dark field illumination configuration employing a strip illuminator 74 (FIG. 3). The stage 46 is inclined at angle β, preferably between 12°–18° relative to the horizontal, away from the tall wall illumination array 70 and toward strip illuminator 74. A blind 94 preferably is provided to adjust the breadth of illumination emanating from strip illuminator 74 to a relatively small strip of between 5 and 12 cm. It is readily appreciated that instead of the blind 94, a narrow illumination source may be employed as strip illuminator 74. It is seen that if an inspected surface 96 supported on stage 46 (FIG. 3) is inclined toward strip illuminator 74, the strip illuminator 74 provides illumination at a sufficiently low angle relative to surface 96 such that the illumination does impinge on lens 84 associated with sensor 48.

It is appreciated that the illumination configurations are preferably determined empirically to maximize the contrast of various types of defects on substrate 24, and to minimize undesired reflections therefrom.

Figure 9:
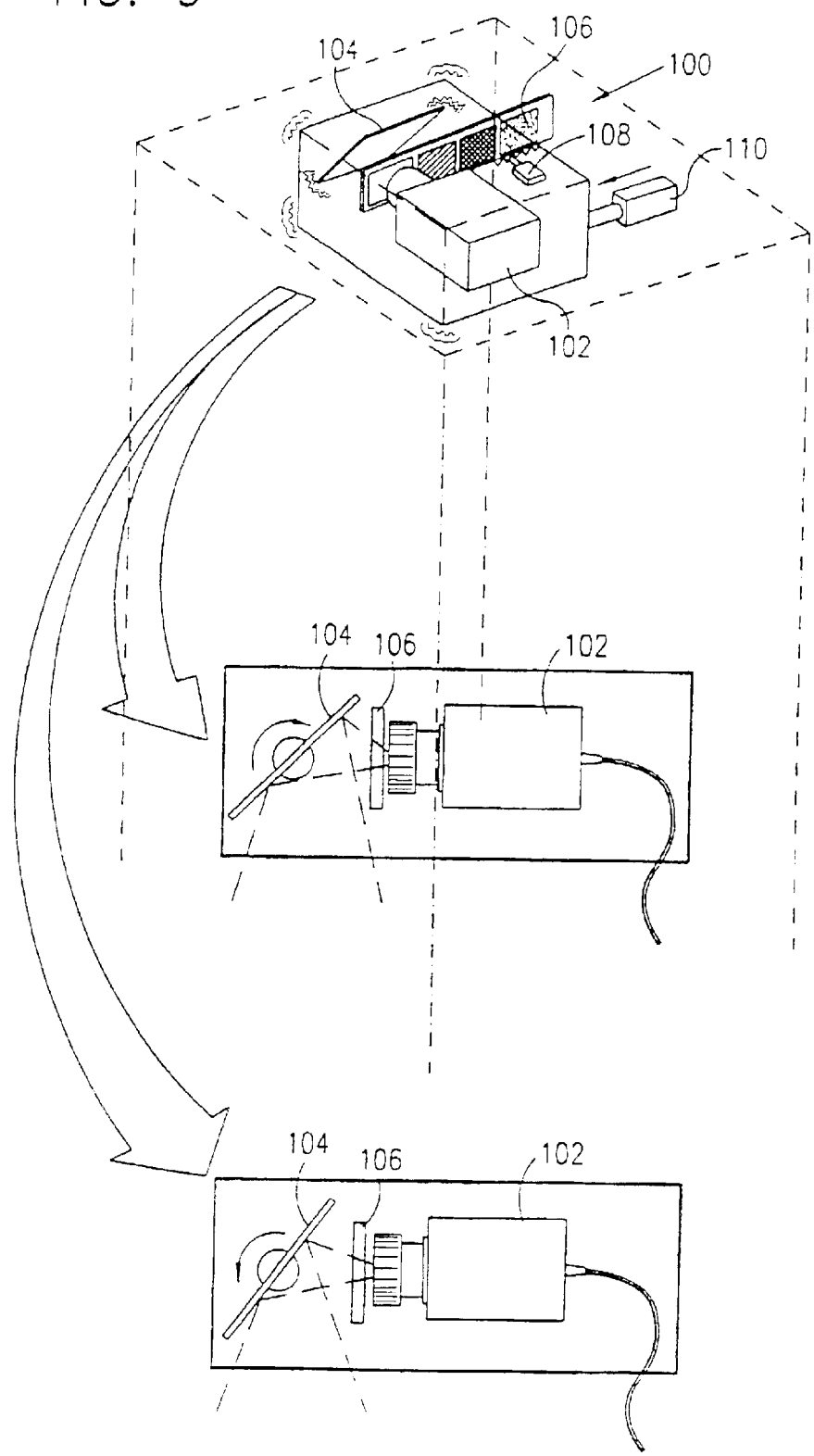
FIG. 9 is a simplified pictorial illustration of the structure and operation of an optical head of a preferred embodiment of the invention.

Reference is now made to FIG. 9, which illustrates the structure of an optical head 100 suitable for use in the present invention. Optical head 100 preferably comprises a non-scanning sensor 102, a mirror 104, a plurality of optical filters 106, a mechanical driver 108 for changing optical filters 106, and a blur generator 110. Preferably, the plurality of filters 106 includes both polarizing filters and spectral filters. A surface of substrate 24 (FIG. 3) is preferably imaged using various different combinations of filters 106 to acquire a series of broad spectrum, narrow spectrum and polarized light images. The angular orientation of mirror 104 may be adjustable as shown, to enable imagine of various parts of the substrate or to minimize reflection of images of optical head 100 by the substrate 24 (FIG. 3).

Preferably, during imaging, blur generator 110 is operative to introduce blurring in the image acquired by sensor 102. Blurring is effective to attenuate the Moire effect arising from resolution differences between sensor 102 and the pattern deposited on the substrate 24 (FIG. 3). The blurring! may be achieved by means of mechanical vibration that is operative to cause relative displacement between sensor 102, and/or mirror 104 and/or stage 46 (FIG. 3) and/or any other suitable optical element situated along the optical path between the sensor and the stage. Alternatively, blurring may be introduced by an optical blurring filter or by other means such as electronic manipulation of the image signal.

Figure 10:
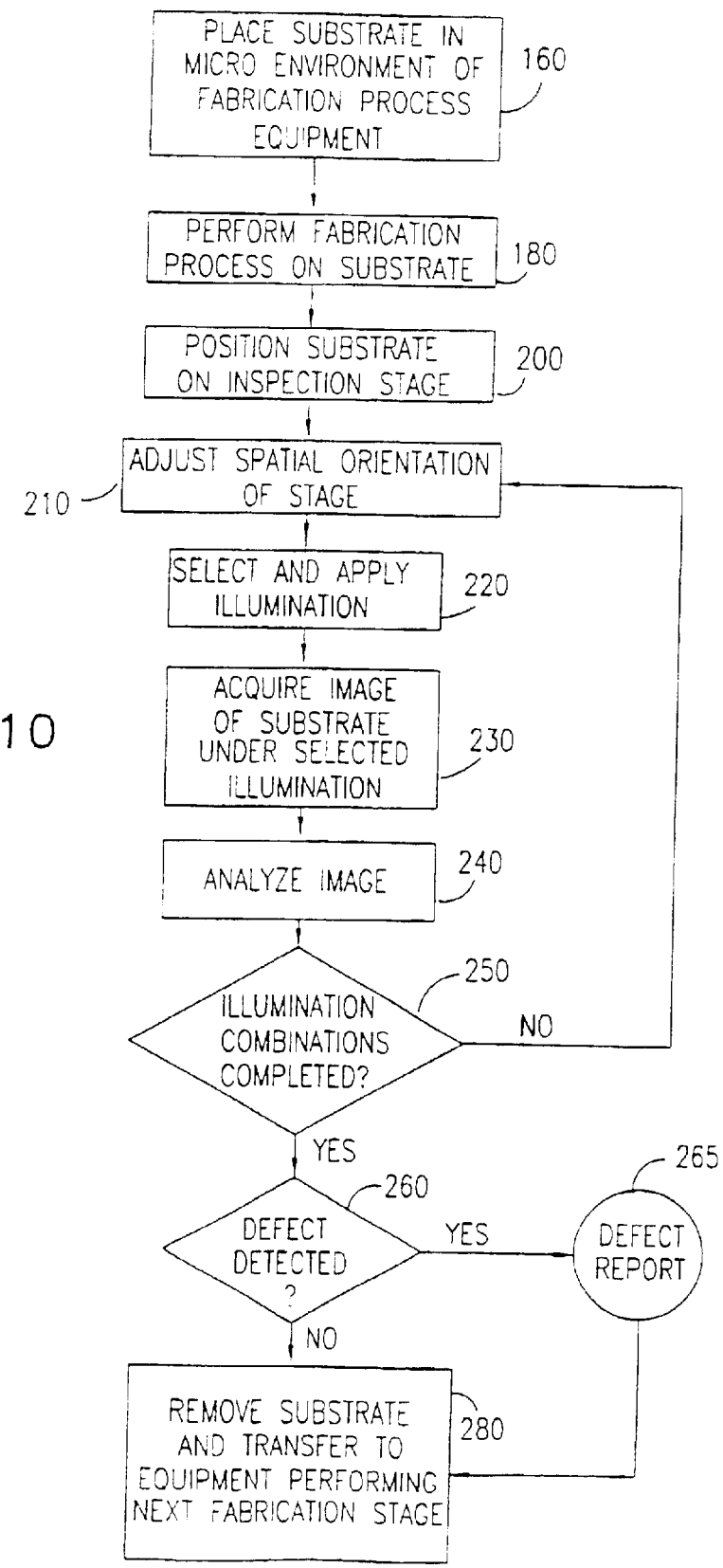
FIG. 10 is a simplified flow chart illustrating operation of a system for generating a patterned coating on a surface of a planar substrate and inspecting the surface in accordance with a preferred embodiment of the invention.

Reference is now made to FIG. 10 which is a flow diagram illustrating the operation of a fabrication equipment and an inspection system, such as the system of FIG. 1, for use in fabricating FPDs. Although the invention is described with reference to the fabrication of FPD's, it is readily appreciated that the invention may be used in the context of applying and inspecting contains to Oat surfaces of other suitable objects and articles. The flow diagram of FIG. 10 shows the steps of performing a fabrication process on a substrate, for example the application of a coating, and inspecting the substrate. The operation illustrated in FIG. 10 preferably identifies fabrication process flaws while an in-fabrication FPD substrate is still within the self-contained environment of fabrication equipment 12 (FIG. 1), and before the substrate is transferred to other equipment that performs downstream fabrication steps.

As shown in FIG. 10, the following steps are preferably performed:

STEP 160: A cassette 20 (FIG. 1) containing FPD substrates 24 (FIG. 3) is placed in fabrication equipment 12 (FIG. 1) that has a self-contained micro environment having a level of airborne contamination substantially lower than the level of airborne contamination in a surrounding clean room 15 (FIG. 1).

STEP 180: A series of fabrication process steps is sequentially performed on the each of substrates 24. By way of example only, a series of steps performed in particular equipment may include the deposition a photoresist film over a thin metallic film previously deposited on a substrate 24, exposure of the photoresist in a predetermined pattern using conventional exposure equipment, subsequent development of the photoresist and washing away unexposed photoresist to leave on the substrate a patterned deposit of photoresist. Alternatively, and other suitable series of predetermined process steps may be performed.

STEP 200: After the completion of various fabrication process steps performed on a substrate 24 in fabrication equipment 12, and prior to its transfer to other fabrication equipment for subsequent fabrication processing, substrate 24 is positioned on stage 46 (FIG. 3) of the inspection system 14, preferably situated inside the self-contained micro-environment of equipment 12. It is readily appreciated that inasmuch as inspection system 14 is situated inside fabrication equipment 12, substrate 24 does not have to be removed from fabrication equipment 12 to be inspected and it is not necessary to wait for the completion of fabrication processes on an entire batch of substrates 24. Thus, preferably, each substrate 24 is inspected immediately upon the completion of a predetermined fabrication process; thus enabling other fabrication processes to continue simultaneously for other substrates in a batch until all substrates have been processed and inspected.

STEP 210: The spatial orientation of stage 46 is adjusted to position the substrate in a predetermined position for bright field illumination or for one of the dark field illumination combinations. To minimize undesired reflections and to aim the field of view of sensor 48 (FIG. 3) to a desired part of substrate 24 that is to be inspected, the angular orientation of mirror 50 (FIG. 3) is adjusted, as necessary.

STEP 220: A predetermined configuration of illumination is applied to substrate 24. The illumination may include the activation of appropriate illumination units 60 (FIG. 3) if diffuse illumination is desired, and may also include the interposition of suitable optical filters 106. The illumination may be in the form of bright field illumination, or any combination of suitable dark field illumination.

STEP 230: An image of the substrate is acquired in a digitized form by sensor 48 and channeled to computer image processor 44 (FIG. 3) through frame grabber hardware (not shown) and software such as a PCI DV frame grabber system, available from EDT, Inc. of Oregon. Preferable, a single full frame image of the substrate is acquired.

STEP 240: The image acquired in step 230 is analyzed for fabrication process defects using image analysis techniques, for example techniques more fully described in U.S. Pat. No. 5,771,068, to the present assignee, the disclosure of which is hereby incorporated by reference. Preferably, these techniques include edge definition and registration functions, and are augmented by fine feature detection techniques for identifying particles and lines such as scratches and rinse tracks. Suitable fine feature detection may be adapted from the ultra fine defect detection described in detail in U.S. Pat. No. 5,586,058, incorporated herein by reference.

It is a particular feature of the preferred embodiments of the image acquisition and analysis system that image analysis is preferably performed without reference to an external reference.

Because a properly fabricated substrate should be comprised of evenly deposited films and should not have any residues, streaks, scratches, particles or other similar anomalies thereon, fabrication process flaws generally can be identified as areas on the substrate whose reflected intensities differ from those of surrounding areas by an amount that is less than or greater than a predetermined deviation threshold.

STEP 250: If additional combinations of illumination are required, steps 210–240 are repeated.

STEP 260: Upon acquisition and analysis of all desired images, a determination is made, using computer image processor 44, whether process defects exist on the substrate. If a defect is found, a defect report 265 issues. The determination may be made for each substrate, and information about defects may be fed into a data base of defects. Substrates found to contain fabrication process defects may be marked as defective and removed for repair or discarded so that further processing resources will not be wasted on a defective substrate until after it is repaired.

The close temporal proximity of detection of fabrication process flaws to completion of a set of process steps provided by the present invention enables close monitoring of the production and control conditions under which equipment 12 fabricates substrates. Thus, computer 44 is preferably programmed to provide an alarm, or in extreme conditions to shut down equipment, when defective substrates are produced.

For example, computer controller and image processor 44 (FIG. 3) may be tailored to selectively provide an alert or shut down the equipment depending on the nature of the flaw. Thus, if a particular flaw, such as a scratch, that necessitates the discarding of affected substrates, occurs in a predetermined number of sequential substrates, such as three substrates, then the computer controller may automatically shut off the defective equipment to prevent production of additional defective substrates. However, if a less critical flaw, for example the presence of a rinse residue, occurs a number of times but non-sequentially then the affected substrates can be set aside for repair and an appropriate alert may be made so that the machine can be repaired or adjusted when convenient.

It is appreciated that the system whose operation is described hereinabove with reference to FIG. 10 provides considerable flexibility in determining the particular combination of conditions under which affected equipment is shut down, or an alert is provided.

STEP 280: Those substrates which have been determined not to be flawed are placed in cassettes and removed from the self-contained micro-environment of the equipment, and are transferred to other equipment for the next stage of processing and inspection. Those substrates which have been classified as having repairable flaws may be transferred to a suitable repair station, before subsequent process stages are performed.

Figure 11:
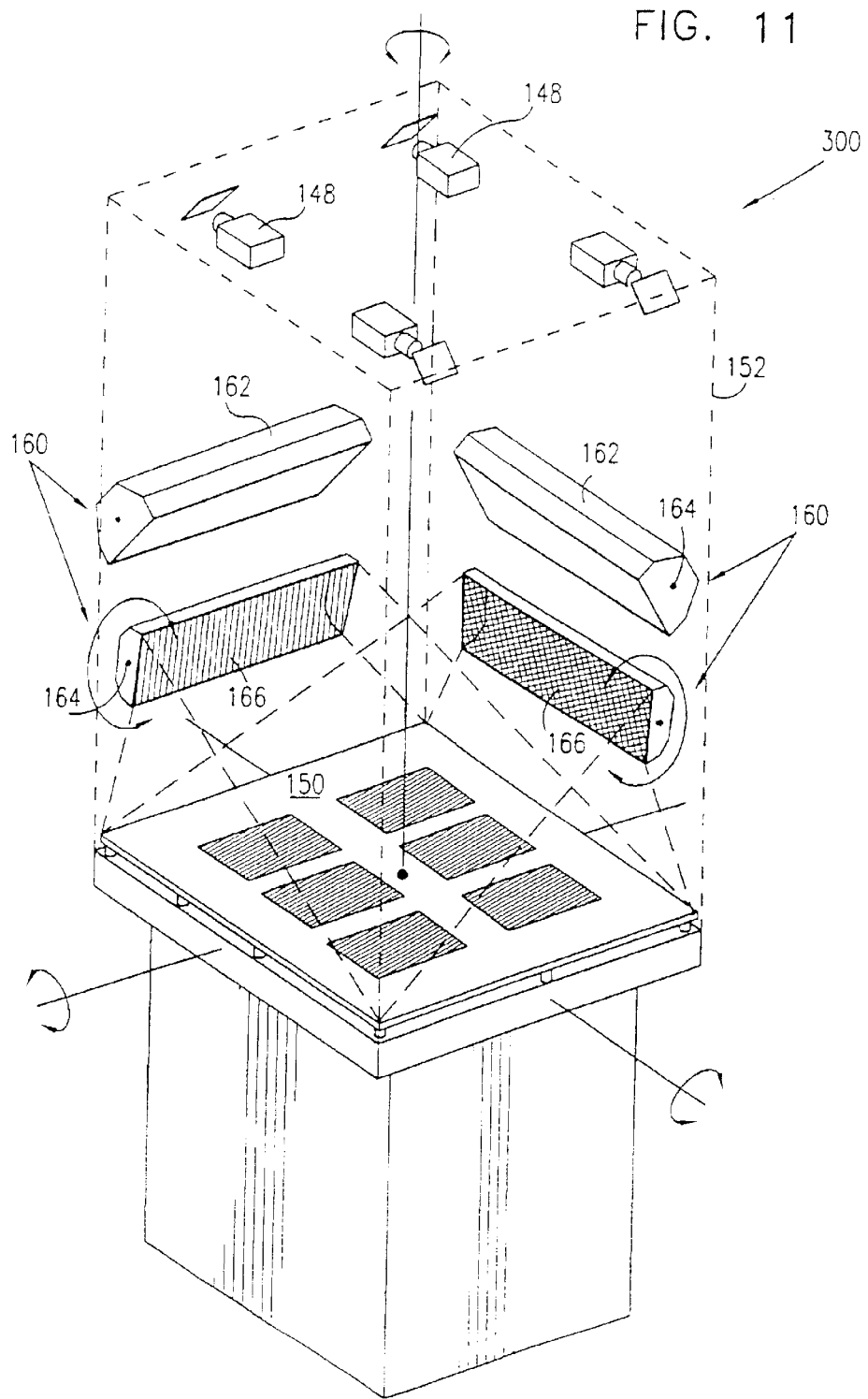
FIG. 11 is a simplified pictorial illustration of various structures for illumination and image acquisition which may be incorporated in an inspection system constructed and operative in accordance with additional preferred embodiments of the present invention.

Reference is now made to FIG. 11 which illustrates some additional features of preferred embodiments of the present invention. Instead of a single sensor 48 as in the embodiment of FIG. 3, here a plurality of non-scanning staring array sensors 148 is shown.

Each of the plurality of sensors 148 preferably images a part of a substrate 150. Images produced by each sensor 148 preferably are stitched together to provide a complete image of substrate 150. This arrangement of sensors 148 enables the processing of a relatively large substrate without compromising resolution and without substantially increasing the height of an enclosure 152, which encloses the inspection region.

Illumination may be provided by illuminators 160. Illuminators 160 are preferably provided with reflectors 162 to direct illumination onto substrate 150, and are preferably pivotably mounted on pivots 164. Drivers (not shown) may be provided to enable tilting of the illuminators 160 and to enable the illumination therefrom to be selectively directed. The illuminators 160 may optionally be provided with diffusers or filters 166.

Figure 12:
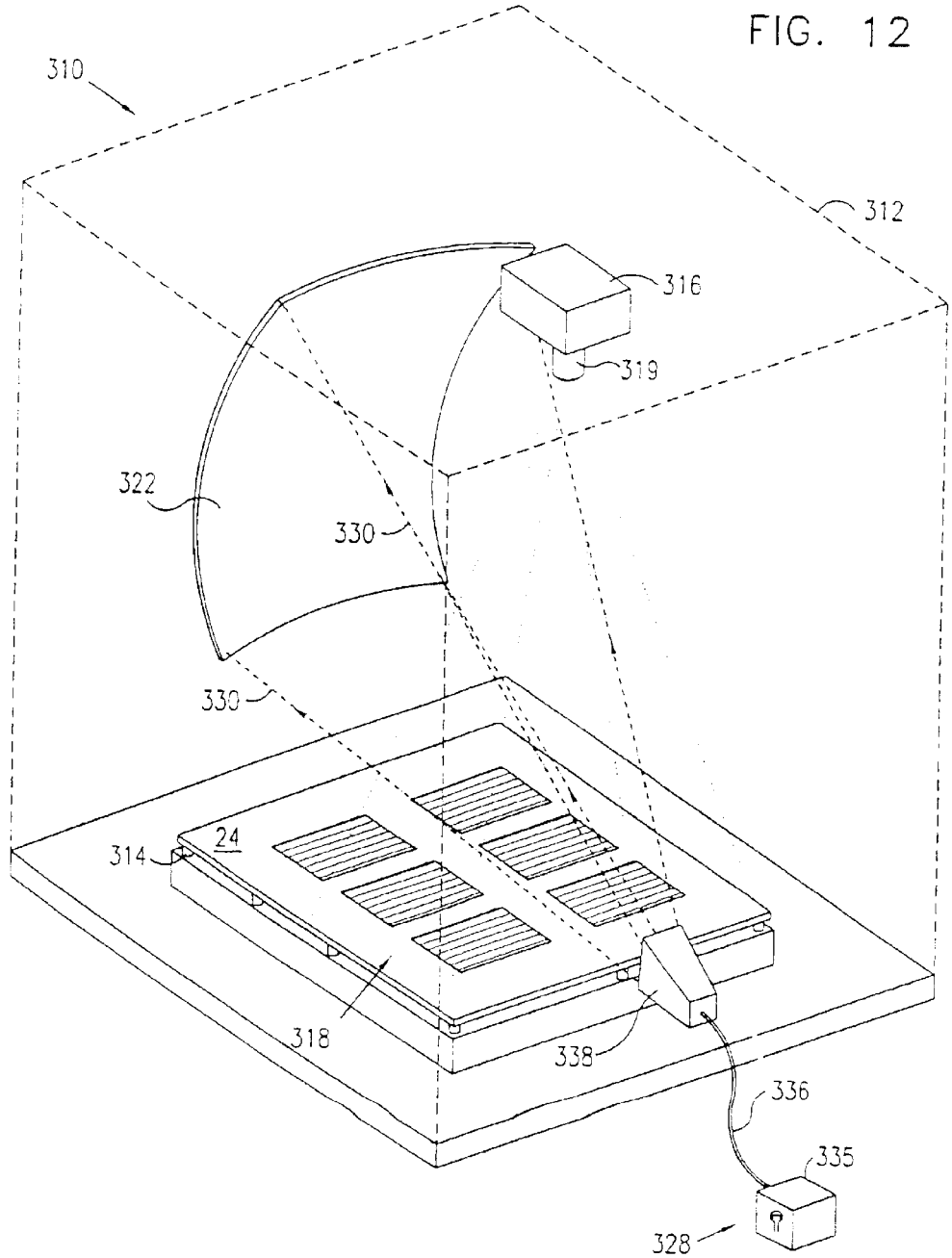
FIG. 12 is a simplified pictorial illustration of an illumination and image acquisition subsystem of an inspection system constructed and operative in accordance with an additional preferred embodiment of the present invention.
Figure 13:
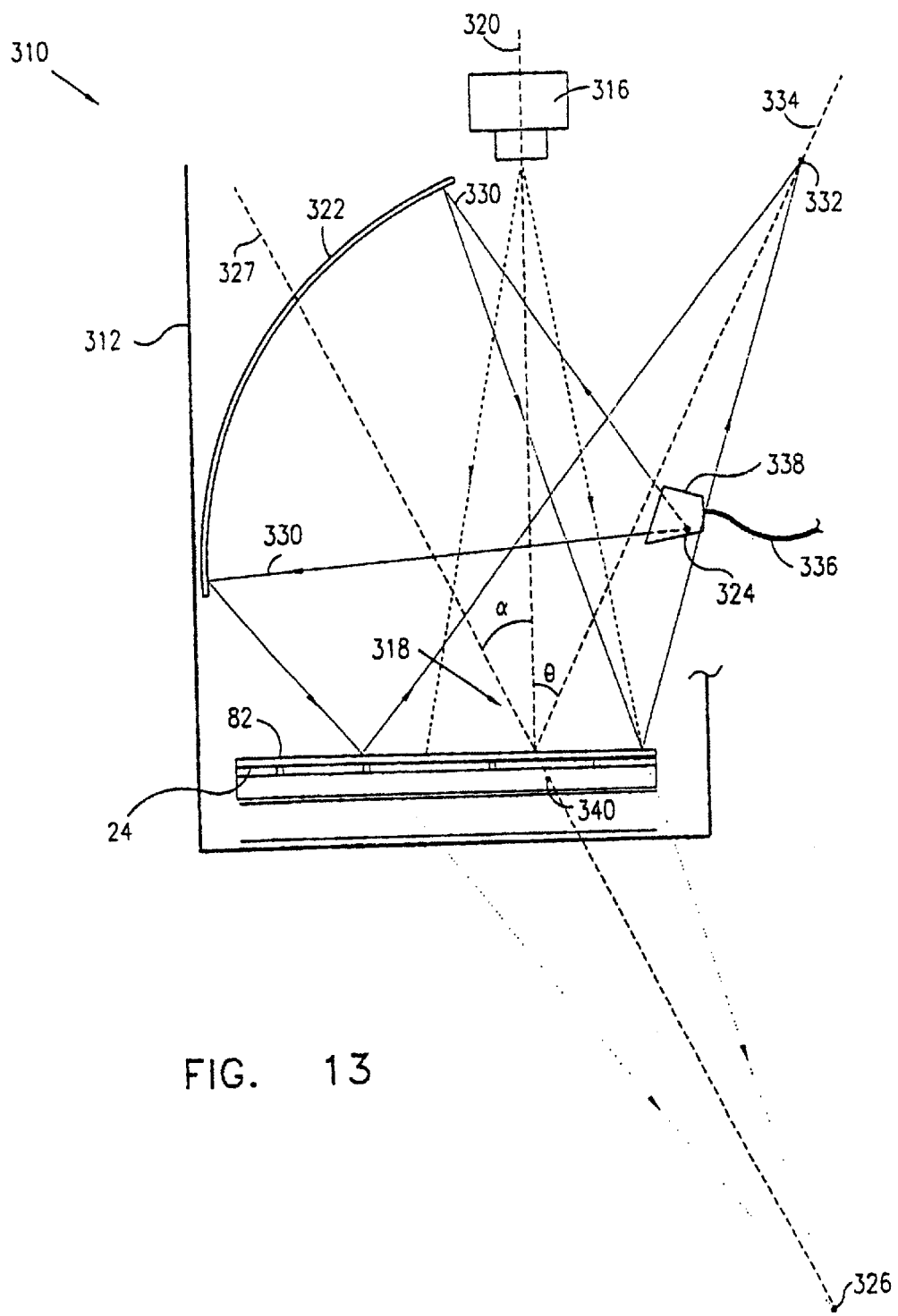
FIG. 13 is a side view of the illumination and image acquisition subsystem shown in FIG. 12.

Reference is now made to FIG. 12 which is a simplified pictorial illustration of an illumination and image acquisition subsystem of an inspection system constructed and operative in accordance with an additional preferred embodiment of the present invention, and to FIG. 13 which is a side view of the illumination and image acquisition subsystem shown in FIG. 12.

In the preferred embodiment shown in FIGS. 12 and 13 an illumination and image acquisition subsystem 310 of an inspection system 14 (FIG. 1), is operative to provide selectable combinations of focussed bright field and focussed dark field illumination to a surface of an article under inspection, such as a surface of in-process FPD substrate 24.

Subsystem 310 preferably comprises a substantially fully enclosed inspection enclosure 312 shown in phantom lines. The width and depth dimensions of inspection enclosure 312 are preferably up to about 160×180 cm so as to accommodate FPD substrates typically having dimensions of about 73×92 cm and to facilitate their rotation about a central axis inside inspection enclosure 312. It is readily appreciated that the above indicated dimensions are representative and are not intended to be limiting and that other dimensions may be employed in order to accommodate various other sizes of substrates. The height of inspection enclosure 312 is preferably up to about 150 cm. Typically, in order to accommodate inspection enclosure 312 inside fabrication equipment 12 (FIG. 1), it is necessary to tilt the inspection enclosure 312 to one side.

A stage 314 is situated in the base of the inspection enclosure 312 for supporting a workpiece, such as an in-fabrication FPD substrate 24, and a non-scanning staring array sensor 316, such as sensor 48 (FIG. 3). Sensor 316 is secured to enclosure 312 overhead of stage 314 and is provided with a suitable lens 319 to view a viewing region 318 along an optical axis 320 (FIG. 13). Viewing region 318 constitutes at least a substantial portion of the surface of substrate 24, and preferably at least one half of substrate 24.

Subsystem 310 preferably includes a concentrating optical element, preferably, a reflector 322 that is preferably formed as a section of an ellipsoid having first and second foci 324 and 326 (FIG. 13). An illuminator 328 is configured and arranged to illuminate reflector 322 from first focus 324 and to provide a substantially uniform beam of high intensity light, represented by rays 330, which are concentrated by reflector 322 to second focus 326. Second focus 326 is preferably located away from the surface of substrate 24 along an illuminating light beam axis 327 which forms an angle α with reference to optical axis 320. The concentrated light provided by the combination of illuminator 328 and reflector 322 is intersected by, substrate 24 to illuminate a region on the surface of substrate 24 that is preferably closely coincidental to viewing region 313 (FIG. 13). As is readily appreciated, the beam represented by rays 330 actually never reaches second focus 326, but rather is reflected by substrate 24, which typically has a substantially specular surface, to a third, virtual, focus 332 which is situated along a reflection axis 334 forming an angle 9 with respect to optical axis 320.

Illuminator 328 preferably includes a light source 335 and fiber optic unit 336, suitably a 250W DC metal halide light box and fiber optic cable available from Mejiro Precision, Inc. of Tokyo Japan, and a projector 338 configured and operative to shape a beam represented by rays 330 and to project it onto reflector 322 so as to substantially fill reflector 322, without overfill.

Reference is now made to FIG. 14 which is a simplified pictorial illustration of illumination and image acquisition subsystem 310 illustrating axes of inclination and rotation of stage 314 and substrate 24 thereon. Operation of the stage is generally self-explanatory in view of the foregoing discussion with reference to FIG. 5, however it is noted stage 314 may be inclined about an axis of inclination 340 that is located substantially along the median of viewing region 318, so that stage 314 forms and angle of inclination β relative to the horizontal. Additionally, stage 314 may be inclined about axis 342 or rotated around axis 344.

Reference is now made to FIGS. 15A-15E which are simplified side view illustrations of illumination and acquisition subsystem 310 showing the effect of changing the angle of inclination β of stage 314 to effect various spatial orientations between stage 314, projector 338 and sensor 316. As is appreciated from the drawings, reflector 322 is illuminated by projector 338. Stage 314 is inclined about axis 340 to form various selectable angles of inclination β with reference to the horizontal. Preferably, reflector 322 is held in stationary orientation relative to projector 338, to receive a beam emitted by projector 338 at first focus 324. Reflector 32 concentrates the beam represented by rays 330 to second focus 326. However, inasmuch as substrate 24 has a specularly reflective surface, such as the glass of an FPD substrate, the beam represented by rays 330 is reflected so that it focuses at third focus 332 located along reflection axis 334.

As the inclination of stage 314 is changed, angle θ between reflection axis 334 and optical axis 320 chances in accordance with the principal that the angle of reflection off of the specular surface of substrate 24 equals the angle of incidence: accordingly the position of third focus 332 moves in space in relation to the angle of inclination β of stage 314. As shown, the inclination of stage 314 may be adjusted to provide focussed bright field illumination (FIG. 15E) in which rays 330 that are specularly reflected impinge on lens 319. The inclination of stage 314 may also be adjusted to provide focussed dark field illumination, in which rays 330 that are specularly reflected are concentrated to focus at a various locations outside lens 319, along a reflection axis 334, at an angle θ to optical axis 320 (FIGS. 15A–15D). Thus, as seen in FIG. 15A, a large positive value of r results in third focus 332 being located at a relatively large distance from sensor 316. As the inclination of stage 314 is reduced, β is reduced and third focus 332 becomes situated closer to sensor 320 (FIG. 15B). The position of third focus 332 is moved closer to sensor 316 when the inclination of stage 314 is made horizontal, for which β=0 (FIG. 15C), and is moved still closer to sensor 316 when the stage 314 inclined below horizontal, for which β is negative (FIG. 15D). Eventually, as stage 314 is further inclined, third focus 332 converges at lens 319 to form focussed bright field illumination (FIG. 15E).

Figure 16B:
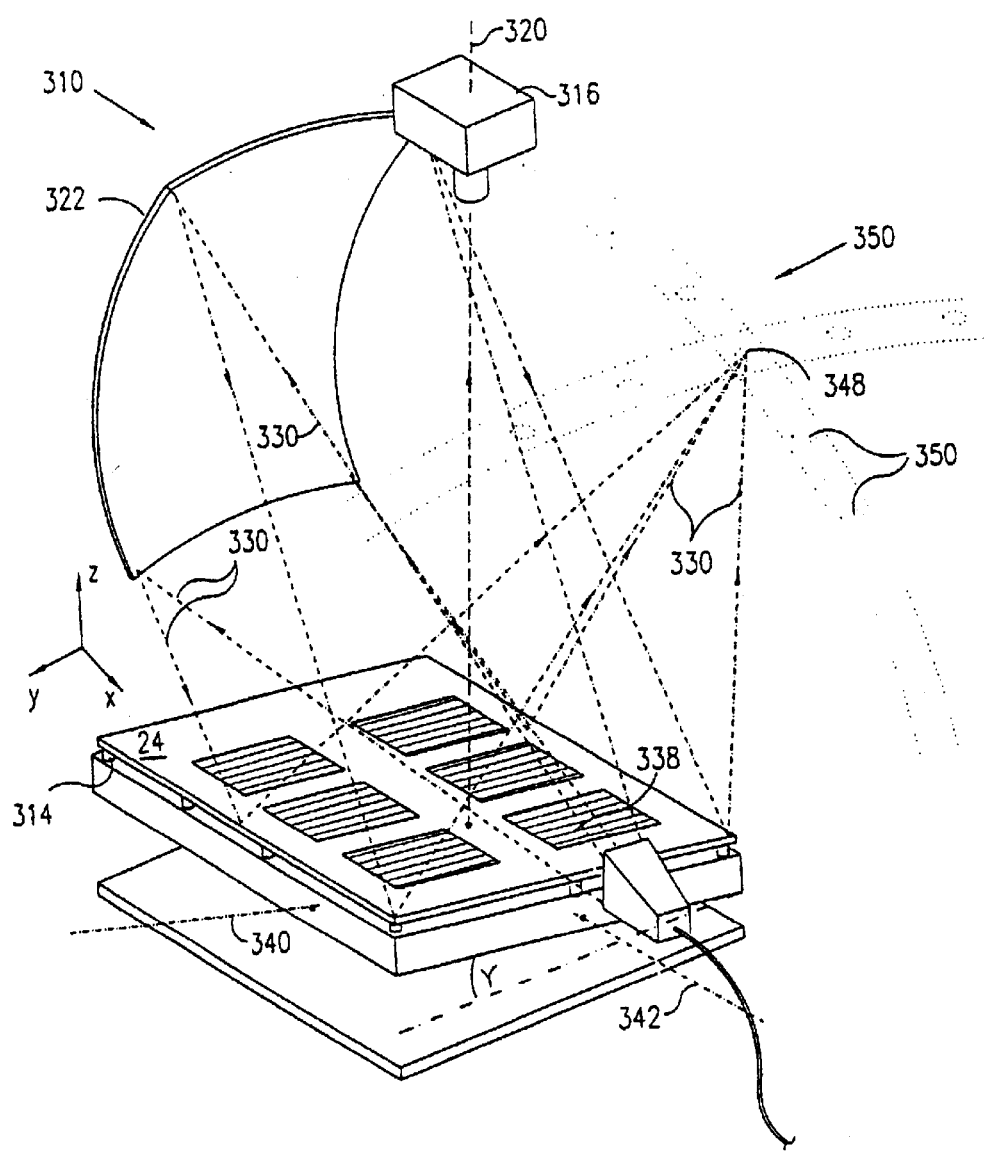

Reference is now made to FIG. 16A and 16B which are simplified pictorial illustrations of illumination and image acquisition subsystem 310 illustrating the effect of diffraction, for example due to a periodic spatial feature on substrate 24, and further illustrating on-axis focussed dark-field and off-axis focussed dark field illumination. It is readily appreciated that the surfaces of substrates typically inspected in inspection system 14, such as FPDs, typically have a dense matrix of liquid crystal cells and conductive connectors which form a two dimensional diffraction grating that diffracts light incident thereon such that diffracted light converges at third focus 332 for a central or zero'th order of diffraction, while other, non-zero, orders of diffraction focus at other focal points in 346.

As seen in FIG. 16A, when stage 314 is in a predetermined spatial orientation, preferably inclined alone axis 340 and substantially horizontal along the axis 342, rays 331 from the zero'th order of diffraction converge to focal point 332 which is situated outside lens 319. Rays from non-zero orders of diffraction (not shown) converge at other focal points 346 along mutually orthogonal axes, and at least one non-zero order 347 impinges on lens 319. The illumination configuration in which the zero'th order of diffraction converges at a focus 332 outside sensor 316 and at least one non-zero'th order of diffraction 347 impinges on lens is designated "on-axis focussed dark field illumination".

It is appreciated that the inclination of stage 314 respective to axis 340 may be adjusted independently of inclination relative to axis 342. Adjustment of the inclination of axis 340 to form non-horizontal angle β, for example as shown in FIGS. 15A, 15B, and 15C, changes the angle θ so that various lower and higher orders of diffraction, respectively, reach lens 319.

It is further appreciated that in focussed bright field illumination, the zero'th order of diffraction impinges on lens 319, and non-zero orders of diffraction are located outside lens 319 (not shown).

Referring now to FIG. 16B, it is seen that when stage 314 is inclined along axis 342 at an angle γ, then rays 331 forming the zero'th order of diffraction converge at a focal point 348 while non-zero'th order diffraction converge at points 350. In this arrangement, rays 331 from the zero'th order of diffraction and all other orders of diffraction, along their respective mutually orthogonal axes, converge at foci outside lens 319; preferably no orders of diffraction impinge on lens 319. The illumination of this arrangement is designated "off-axis focussed dark field illumination".

Figure 17A:
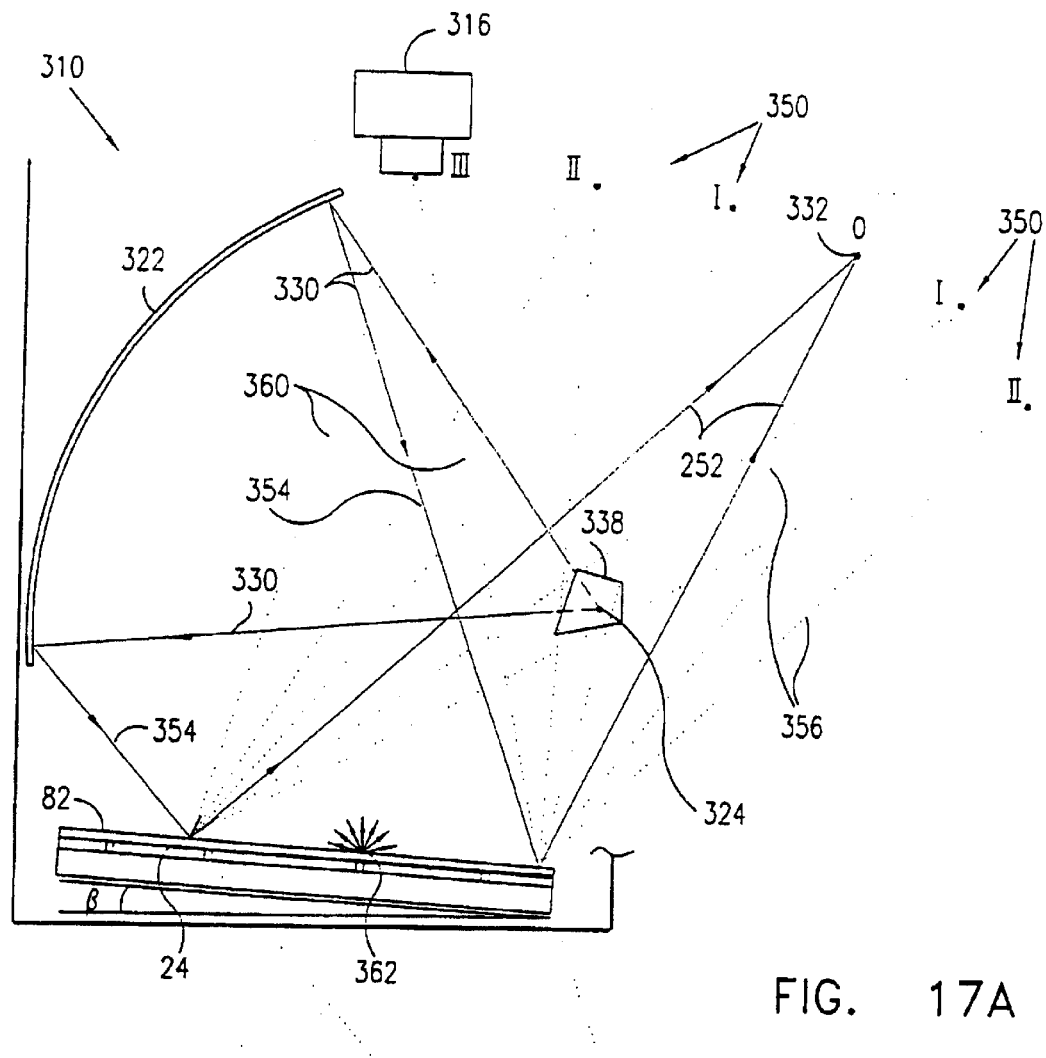

Reference is now made to FIG. 17A which is a simplified side view illustration of diffraction occurring in the illumination and image acquisition subsystem 310 which provides focussed dark field illumination as described with reference to FIGS. 12-16B, and to FIG. 17B which is a simplified side view illustration of the illumination and image acquisition subsystem 410 that provides diffuse dark field illumination, such as is provided by a preferred embodiment described above with reference to FIGS. 6-8.

As seen in FIG. 17A, in an illumination and image acquisition system 310 which provides focussed illumination, for a clean surface 82 which is free of defects, diffracted rays 352 from a zero'th, or central order of diffraction, designated "0", all converge at third focus 332, preferably independent of the location where projected rays 330 from the projector 338 impinge on reflector 322 or where rays 354 impinge on surface 82 of substrate 24. Likewise, for a clean surface 82 which is free of defects, diffracted rays 356 from other non-zero'th, orders of diffraction mutually converse at other focal points 350 as a function of the order of diffraction. Thus rays from the same or similar orders of diffraction, such as diffracted rays 356 from each of the diffraction orders I, II and III shown in FIG. 17A, by way of example only, generally converge each at the same regions in space independent of the location where projected rays 330 impinge on reflector 322, or where reflected rays 354 impinge on surface 82 of substrate 24.

For defects on surface 82, such as defect 360, reflected light is typically scattered, thus resulting in scattered rays 362 being reflected differently than diffracted rays 352 and 356, which typically results in a difference in light intensity for defect 362, relative to its surroundings, as viewed by sensor 316.

Referring now to in FIG. 17B, it is seen that in illumination and image acquisition system 410 which provides diffuse illumination, rays 412 emitted by the diffuse illuminator 413 are emitted in various directions from illuminator 413. As a result, rays 415 from a first point of illumination 416 impinge on substrate 24 at various different locations and at various different angles of incidence. At each location on substrate 24 illuminated by first point of illumination 416, rays 418 from other points of illumination, such as point 420, also impinge on substrate 24 at a various and different angles of incidence.

The effect of the differing angles of incidence emitted from the diffuse illuminator 413 is that the zero'th, or central, orders of diffraction, shown as rays "0", and all other orders of diffraction, shown as orders I, II, III and IV, are diffracted in various and different directions. Consequently, in the diffuse illumination configuration of subsystem 410, various orders of diffraction, exemplified by orders "0", "I", "II", "III" and "IV", rather than a single order of diffraction, or nearly similar orders of diffraction, enter a lens 421 which is associated with a sensor 422.

A defect (not shown) on surface 82 of substrate 24 will typically be seen as a variation in reflective intensity in relation to its surroundings, although the variation may not be as pronounced as in the system shown in FIG. 17A.

In accordance with a preferred embodiment of the present invention, multiple images of substrate are acquired. Each image is acquired using a different configuration of illumination, preferably a focussed bright field illumination and various configurations of focussed dark field illumination. A preferable image acquisition sequence may include the following combination of illumination configurations: Focussed on-axis dark field illumination for a values of 15°, 20°, 35°, 50° and 70°. Focussed off-axis dark field illumination for θ0 values of 70°, and stage 314 inclined along axis 342 to an angle γ value of 10°; Focussed bright field illumination through a narrow band optical filter permitting transmission of a narrow bandwidth of light Δλ=±10 nanometers, for wavelength visible to sensor 316. Preferably, the above sequence, in whole or in part is repeated with stage 314 rotated 90°, 180° and 270° about axis 344 respectively.

Figure 18:
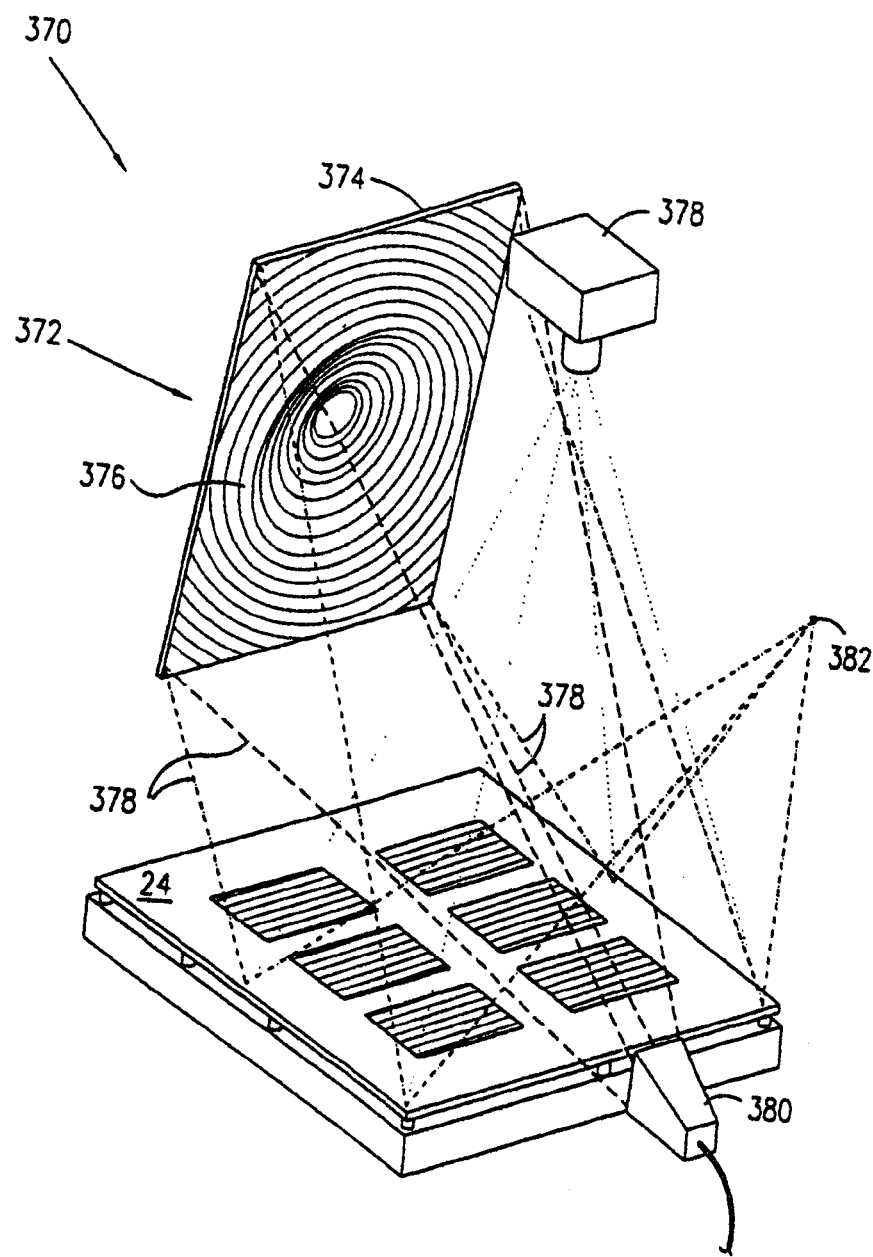
FIG. 18 is a simplified pictorial illustration of an illumination and image acquisition subsystem of an inspection system constructed and operative in accordance with still another preferred embodiment of the present invention, employing a fresnel lens and reflector assembly.

Reference is now made to FIG. 18 which is a simplified pictorial illustration of an illumination and image acquisition subsystem of an inspection system constructed and operative in accordance with still another preferred embodiment of the present invention employing a fresnel lens and reflector assembly. In accordance with the preferred embodiment illustrated in FIG. 18, illumination and image acquisition subsystem 370 is configured and arranged to provide focussed dark field and focussed bright field illumination, and is similar in construction and operation to illumination and image acquisition subsystem 310 illustrated in FIGS. 12-16B.

Illumination and image acquisition subsystem 370 differs from illumination and image acquisition subsystem 310 in that it includes a reflector assembly 372 which is constructed from a planar reflector 374 and a concentrating lens 376, preferably a fresnel lens, which is mounted directly on planar reflector 374. Reflector assembly 372 is preferably configured to emulate operation of an elliptical reflector so as to receive a beam of light, represented by rays 378, from projector 380, which is generally situated at a first focus of reflector assembly 372, and to reflect the light beam represented by rays 378 to a second focus of reflector assembly 372. Substrate 24 intersects the light beam represented by rays 378 so that specularly reflected rays 378 converge at a focus 382 at distance from projector 380.

Figure 19:
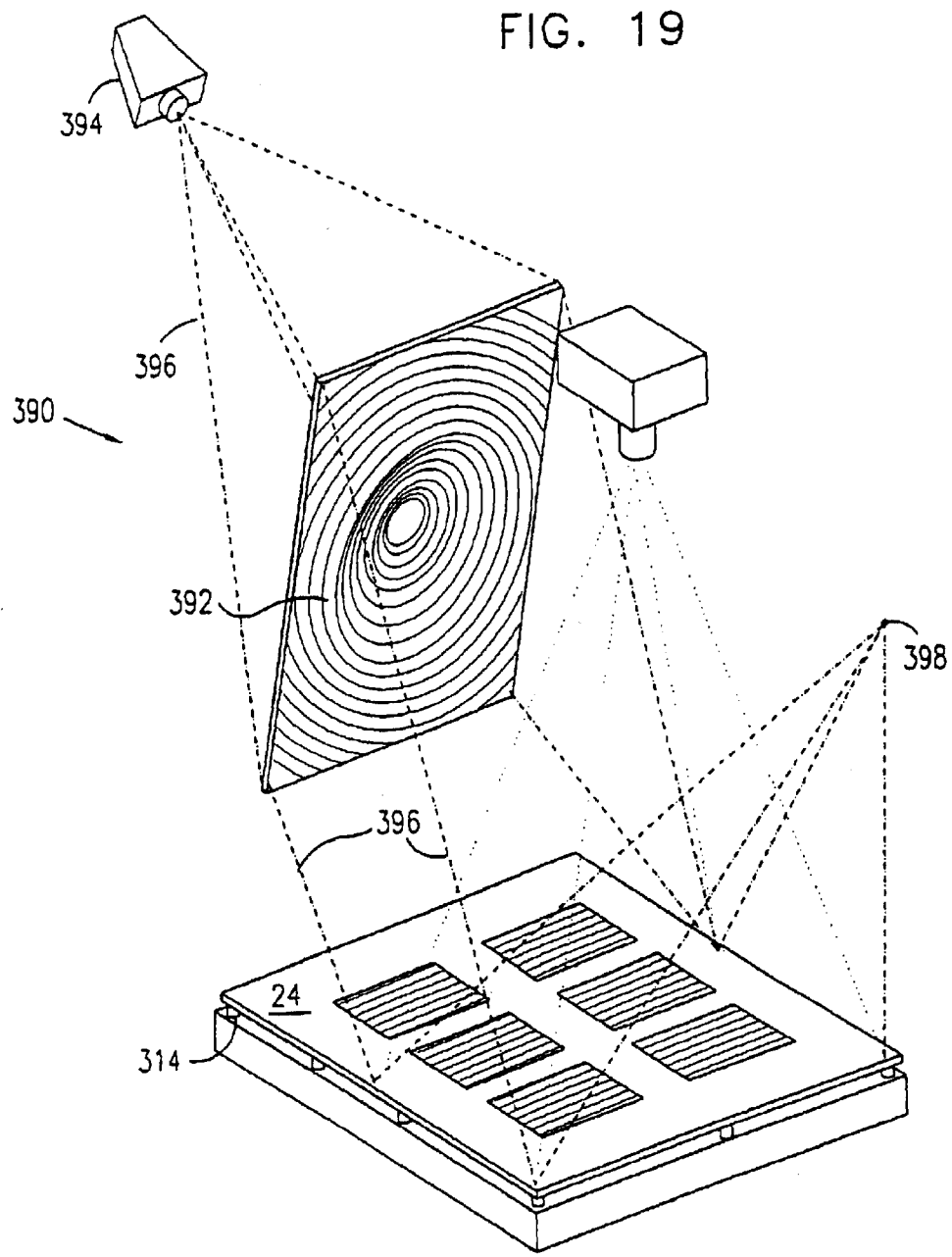
FIG. 19 is a simplified pictorial illustration of an illumination and image acquisition subsystem of an inspection system constructed and operative in accordance with yet another preferred embodiment of the present invention, employing a transmissive fresnel lens.

Reference is now made to FIG. 19 which is a simplified pictorial illustration of an illumination and image acquisition subsystem 390 of an inspection system constructed and operative in accordance with still another preferred embodiment of the present invention employing a transmissive fresnel lens. In accordance with the preferred embodiment illustrated in FIG. 19, illumination and image acquisition subsystem 390 is configured and arranged to provide focussed dark field and focussed bright field illumination.

Illumination and image acquisition subsystem 390 includes a lens 392, preferably a fresnel lens. Projector 394 is located at a first focus located one side of lens 392. Lens 392 concentrates light emitted by projector 394, represented by rays 396, and substrate 24 intersects the concentrated light so that specularly reflected rays converge at a focus 398.

Reference is now made to FIG. 20, which illustrates another preferred embodiment of the present invention. In the embodiment of FIG. 20, an inspection system 400 constructed and operative in accordance with a preferred embodiment of the present invention, such as any of the systems shown and described with reference to FIGS. 3-19, is preferably located inside a self-contained ultra-clean micro environment 402 of fabrication equipment 404, which is located inside a clean room area 406 of a fabrication facility, such as fabrication facility 10 (FIG. 1). It is a particular feature of this embodiment that the inspection system is connected to a control unit 408, situated outside the clean room area 406, preferably by means of a cable 410. Control unit is preferably manually operated by a human operator, preferably using a display 412.

As seen in FIG. 20, images of FPD substrates acquired by a sensor in the inspection system 400, may be viewed on display 412, and illumination combinations and camera substrate angles may be determined by a set routine or controlled by the operator, for example by using a joystick 414, other suitable spatial positioning device, or by choosing positions from a predetermined set. It is appreciated, that the inspection system of FIG. 20 provides for close human control of fabrication and inspection by a remotely located operator, and represents a dramatic improvement over systems that require the physical presence of numerous human inspectors inside clean room areas.

It is appreciated that the particular embodiments described herein are intended to be a detailed disclosure of the invention, and are not intended to be limiting. While various of the features have been described for clarity in the context of separate embodiments, these features may also be provided in a single embodiment. Conversely, various features which have been described in the context of a single embodiment may also be provided separately or in a suitable alternative combination.

It should be also be appreciated by persons skilled in the art that the present invention is not limited to what has been particularly shown and described hereinabove. Rather, the scope of the present invention includes combinations and subcombinations of various features described hereinabove as well as modifications and additions thereto which would occur to a person of skill in the art upon reading the foregoing description and which are not in the prior art.

What is claimed is:

1. An inspection system for use in inspecting flat panel displays comprising:
   an optical array including a staring array optical sensor for viewing a flat panel display substrate; and
   an illumination subsystem sequentially providing dark field and bright field illumination of said flat panel display substrate when said optical array views at least a part of said flat panel display substrate.

2. An inspection system according to claim 1 and wherein said illumination subsystem provides various combinations of dark field and bright field illumination of said flat panel display substrate when said optical array views said flat panel display substrate.

3. An inspection system according to claim 2 and wherein said dark field and said bright field illumination are diffuse.

4. An inspection system according to claim 2 and wherein said dark field and said bright field illumination are focussed.

5. An inspection system according to claim 4 and wherein said flat panel display substrate has a surface that includes a periodic spatial feature, and said dark field and said bright field illumination are diffracted by said spatial feature.

6. An inspection system according to claim 2 and also comprising a spatially positionable stage to support the flat panel display substrate, wherein the stage spatially positions the substrate at various angles relative to the illumination subsystem.

7. An inspection system according to claim 6 and wherein the optical array, illumination subsystem and stage are configured and arranged to selectively enable viewing the flat panel display substrate such that a non-zero'th order of diffraction impinges on the staring array optical sensor.

8. An inspection system according to claim 7 and wherein a multiplicity of the non-zero'th orders of diffraction impinge on said staring array optical sensor.

9. An inspection system according to claim 7 and wherein the optical array, the illumination subsystem and the stage are configured and arranged to additionally enable selectively viewing the flat panel display substrate such that a zero'th order of diffraction impinges on the staring array optical sensor.

10. An inspection according to claim 7 and wherein the optical array the illumination subsystem and the stage are configured and arranged to additionally enable selective viewing of the flat panel display substrate such that substantially no orders of diffraction impinge on the staring array optical sensor.

11. An inspection system according to claim 10 and wherein the optical array and the illumination subsystem are configured and arranged to sequentially view the flat panel display substrate and wherein in one view a selected non-zero'th order of diffraction impinges on the optical array, and in other each sequential views at least one of the following impinges on the optical array: a zero'th order of diffraction, an additional selected non-zero'th order of diffraction, no order of diffraction, the same non-zero'th order of diffraction of a different region of the article.

12. An inspection system according to claim 1 and also comprising an image analyzer receiving an output from said staring array optical sensor and being operative to detect process defects including at least one of: uneven deposition of coatings, uneven removal of coatings, rinse residues, chemical residues, incomplete exposure of a photo-resist deposited on the substrate, scratches, lines, and particles embedded in the substrate.

13. An inspection system according to claim 2 and wherein said optical array views substantially all of a surface of said substrate.

14. An inspection system according to claim 2 and wherein said optical array views only part of a surface of said substrate.

15. An inspection system according to claim 2 and wherein said optical array acquires at least one image of said substrate for each of a plurality of different illuminations.

16. An inspection system according to claim 12 in which an image analyzer identifies said defects by computer analysis of a plurality of images of said substrate taken under differing illumination.

17. An inspection system according to claim 2 and also comprising a light source and a reflector operative to provide concentrated light from the light source to at least part of said flat panel display substrate.

18. An inspection system according to claim 17 wherein said reflector has two points of focus, and wherein a projector is situated at a first of points of focus, and the second point of focus is situated away from the flat panel display substrate.

19. An inspection system according to claim 18 and wherein the reflector is a section of an ellipsoid.

20. An inspection system according to claim 18 and wherein the reflector is flat and is operatively associated with a lens.

21. An inspection system according to claim 18 and wherein the lens is a fresnel lens attached to the reflector.

22. An inspection system according to claim 2 and comprising an adjustable mounting assembly for selectable determining at least one of relative inclination, spatial separation and axial orientation of at least two of said optical array, said illumination subsystem and said substrate.

23. Apparatus for optically inspecting a substantially planar surface of an article, comprising:

an inspection region;

an illuminator configuration to selectably illuminate a substantially planar surface of an article located in the inspection region with one of at least two predetermined configurations of illumination, a first configuration of illumination providing dark field illumination and a second configuration of illumination providing bright field illumination;

an image acquisition sub-system comprising at least one camera having a two dimensional field of view for acquiring images of generally the entire surface of the article when illuminated by at least one of said predetermined configurations of illumination; and an image analysis subsystem for computer analysis of the images and detecting anomalies in the surface as a function of variations in reflected intensities of illumination.

24. Apparatus for optically inspecting the surface of an article according to claim 23 and also comprising a spatially positionable stage for supporting the article in the inspection region in selectable orientation relative to the illumination apparatus.

25. Apparatus for optically inspecting the surface of an article according to claim 23, wherein the image analysis subsystem is operative to identify anomalies that are substantially at least as large as the resolution of the camera.

26. Apparatus for coating an article having a substantially planar surface, comprising:

a coating generator operative to generate a coating on a surface of the article;

an illuminator configured to selectably illuminate said surface bearing said coating with one of at least two predetermined configurations of illumination, a first configuration of illumination providing dark field illumination and a second configuration of illumination providing bright field illumination;

an image acquisition sub-system comprising at least one sensor having a two dimensional field of view for acquiring images of generally the entire surface of the article for each combination of illumination; and an image analysis subsystem for analyzing the images and detecting anomalies in the surface on the basis of variations in reflected intensities of illumination.

27. A method for inspecting flat panel displays comprising:

viewing a flat panel display substrate using an optical array, including a staring array camera; and sequentially illuminating said flat panel display substrate with dark field and bright field illumination when said optical array views said flat panel display substrate, to obtain darkfield and brightfield images for substantially the entire flat panel display substrate.

28. A method according to claim 27 and wherein said sequentially illuminating step illuminates using various combinations of dark field and bright field illumination of said flat panel display substrate when said optical array views said flat panel display substrate.

29. A method according to claim 28 and also comprising: supporting the substrate with a spatially positionable stage, and spatially positioning the stage at various angles to illuminate the substrate with dark field and bright field illumination.

30. A method according to claim 28 and also comprising: receiving an output from said staring array camera; and detecting process defects including at least one of: uneven deposition of coatings, uneven removal of coatings, rinse residues, chemical residues, incomplete exposure of a photo-resist deposited on the substrate, scratches, lines, and particles embedded in the substrate.

31. A method according to claim 27 and wherein said viewing step comprises viewing substantially all of a surface of said substrate.

32. A method according to claim 27 and wherein said viewing step comprises acquiring at least one image of said substrate for each of a plurality of different illuminations.

33. A method according to claim 30 and wherein said detecting step comprises identifying said defects by computer analysis of a plurality of images of said substrate taken under differing illumination.

34. A method according to claim 27 and also comprising providing an enclosure containing a first plurality of illuminators mounted on one wall thereof and a second plurality of illuminators mounted on a second wall thereof.

35. A method according to claim 34 and wherein said providing step also comprises providing a third illuminator mounted on a third wall of said enclosure.

36. A method according to claim 27 and also comprising providing a diffuser associated with said illumination subsystem.

37. A method according to claim 27 and also comprising providing an adjustable mounting assembly for selectably determining at least one of relative inclination, spatial separation and axial orientation of at least two of said optical array, said illumination subsystem and said substrate.

38. A method for inspecting objects comprising:

a) viewing a first location on an object using an optical array comprising a staring array sensor;

b) sequentially illuminating said first location with dark field and bright field illumination when said optical array views said object; and c) repeating operations (a) and (b) to obtain images illuminated by said dark field and bright field illumination for additional locations together comprising substantially the entire object.

39. A method according to claim 38 and wherein said sequentially illuminating step illuminates using various combinations of dark field and bright field illumination of said object when said optical array views said object.

40. A method according to claim 39 and also comprising: receiving outputs from said optical array; and detecting process defects including at least one of: uneven deposition of coatings, uneven removal of coatings, rinse residues, chemical residues, incomplete exposure of a photo-resist deposited on the substrate, scratches, lines, and particles embedded in the substrate.

41. A method according to claim 38 and wherein said viewing comprises viewing substantially all of a surface of said object.

42. A method according to claim 38 and wherein said viewing comprises acquiring at least one image of said object for each of a plurality of different illuminations.

43. A method according to claim 40 and wherein said detecting comprises identifying said defects by computer analysis of a plurality of images of said object taken under differing illumination.

44. A method according to claim 38 and also comprising providing an enclosure containing a first plurality of illuminators mounted on one wall thereof and a second plurality of illuminators mounted on a second wall thereof.

45. A method according to claim 44 and wherein said providing step also comprises providing a third illuminator mounted on a third wall of said enclosure.

46. A method according to claim 38 and also comprising providing a diffuser associated with said illumination subsystem.

47. A method according to claim 38 and also comprising providing an adjustable mounting assembly for selectably determining at least one of relative inclination, spatial separation and axial orientation of at least two of said optical array, said illumination subsystem and said object.

48. A method for optically inspecting the surface of an article having a substantially planar surface, comprising:
   a) defining an inspection region;
   b) sequentially illuminating a surface of an article located in the inspection region with at least two predetermined configurations of illumination, a first configuration of illumination providing dark field illumination and a second configuration of illumination providing bright field illumination;
   c) acquiring images of the surface of the article when illuminated by at least one predetermined configuration of illumination using at least one staring array camera;
   d) moving said article or said camera so that a next part of said surface is located in said inspection region and repeating operations (b) & (c) until images of substantially all of said surface are acquired; and
   e) analyzing the images and detecting anomalies in the surface as a function of variations in reflected intensities of illumination.

49. A method for optically inspecting the surface of an article according to claim 48, and also comprising supporting the article on a spatially positionable stage in the, inspection region, and selectably spatially orienting the stage relative to a predetermined configuration of illumination.

50. A method for optically inspecting the surface of an article according to claim 48, wherein said analyzing is operative to identify anomalies that are substantially the same size as the resolution of the said staring array camera.

51. A method for coating an article having a substantially planar surface, comprising:
   generating a coating on a surface of the article;
   sequentially illuminating said surface bearing said coating with at least two predetermined configurations of illumination, a first configuration of illumination providing dark field illumination and a second configuration of illumination providing bright field illumination;
   acquiring images of the surface of the article for each combination of illumination using at least one staring array sensor; and
   analyzing the images and detecting anomalies in the surface on the basis of variations in reflected intensities of illumination.

52. A method for inspecting the surface of an article, comprising the steps of:
   placing the article in an inspection region defined by a stage;
   illuminating a portion of the surface of the article with at least one configuration of dark field illumination;
   acquiring at least one image illuminated under said at least one configuration of dark field illumination, said at least one image covering substantially the entire surface;
   illuminating the surface with at least one configuration of at least substantially bright field illumination;
   acquiring at least one image, said at least one image covering substantially the entire surface, illuminated under said at least one configuration of at least substantially bright field illumination; and
   analyzing the images by computer to determine non uniformities in reflected intensities.

53. The method of claim 52 in which the at least one configuration of dark field illumination comprises a plurality of dark field illumination combinations, and separate images are acquired for each of the combinations.

54. The method of claim 52 in which the at least one configuration of substantially bright illumination comprises a plurality of bright field illumination combinations, and separate images are acquired for each of the combinations.

55. The method of claim 54 comprising the additional step of selecting for each predetermined combination of illumination a predetermined inclination and orientation of the substrate, and acquiring separate images of the surface for each said inclination and axial orientation.

56. The method of claim 52 comprising the additional step of optically treating the illumination prior to acquiring an image.

57. The method of claim 56 in which the treatment is provided by optical filters.

58. The method of claim 57 in which the optical filters filter light at all but selected wavelengths.

59. The method of claim 57 in which the filters filter light to transmit light having a selected polarization.

60. The method of claim 56 in which the surface is illuminated with a selected combination of broad spectrum illumination and imaged through an optical filter operative to transmit light in a first predetermined spectral range, and subsequently imaged through an optical filter operative to transmit light in a second predetermined spectral range.

61. The method of claim 56 in which the surface is illuminated with a first combination illumination provided in first predetermined spectral range and imaged, and subsequently illuminated with a second combination of illumination provided in a second predetermined spectral range and imaged.

62. The method of claim 56 in which the surface is illuminated with a selected combination of broad spectrum illumination and imaged through an optical filter operative to transmit light in a first predetermined polarization, and subsequently imaged through an optical filter operative to transmit light having a predetermined polarization.

63. The method of claim 56 in which the surface is illuminated with a first combination of illumination having a first predetermined polarization and imaged, and subsequently illuminated with a second combination of illumination having a second predetermined polarization and imaged.

64. The method of claim 52 comprising the additional step of blurring the image during acquisition.

65. The method of claim 64 in which the at least one image is blurred by introducing relative movement between at least two of the following: the surface, the camera, and an optical element between the surface and the camera.

66. The method of claim 52 comprising the further step of analyzing said nonuniformities by computer to determine the presence of defects in coatings on the substrate.

67. The method of claim 52 in which the article is a flat display panel substrate.

68. A method for coating the surface of an article with a film, comprising:
   depositing a film coating on at least part of a surface of the article;
   placing the article in an inspection region;
   illuminating a portion of the coated surface of the article with at least one configuration of dark field illumination;

acquiring an image of the surface illuminated by the at least one configuration of dark field illumination;

illuminating the surface with at least one configuration of substantially bright field illumination;

acquiring an image of the entire surface illuminate by the least one configuration of substantially bright field illumination; and analyzing each image by computer to determine non uniformities in reflected intensities.

69. A method according to claim 27 and wherein said dark field and said bright field illumination are diffuse.

70. A method according to claim 27 and wherein said dark field and said bright field illumination are focussed.

71. A method according to claim 70 and wherein said flat panel display substrate has a surface that includes a periodic spatial feature, and said dark field and said bright field illumination are diffracted by said spatial feature.

72. A method according to claim 28 and wherein the optical array, illumination subsystem and stage are configured and arranged to selectively enable viewing the flat panel display substrate such that a non-zero'th order of diffraction impinges on the staring array camera.

73. A method according to claim 72 and wherein a multiplicity of the non-zero'th orders of diffraction impinge on said staring array camera.

74. A method according to claim 72 and wherein the optical array, the illumination subsystem and the stage are configured and arranged to additionally enable selectively viewing the flat panel display substrate such that a zero'th order of diffraction impinges on the staring array camera.

75. A method according to claim 72 and wherein the optical array the illumination subsystem and the stage are configured and arranged to additionally enable selective viewing of the flat panel display substrate such that substantially no orders of diffraction impinge on the staring array camera.

76. A method according to claim 75 and wherein the optical array and the illumination subsystem are configured and arranged to sequentially view the flat panel display substrate and wherein in one view a selected non-zero'th order of diffraction impinges on the optical array, and in other each sequential views at least one of the following impinges on the optical array: a zero'th order of diffraction, an additional selected non-zero'th order of diffraction, no order of diffraction, the same non-zero'th order of diffraction of a different region of the article.

77. A method according to claim 27 and also comprising providing a light source and a reflector operative to provide concentrated light from the light source to at least part of said flat panel display substrate.

78. A method according to claim 77 wherein said reflector has two points of focus, and wherein a projector is situated at a first of points of focus, and the second point of focus is situated away from the flat panel display substrate.

79. A method according to claim 78 and wherein the reflector is a section of an ellipsoid.

80. A method according to claim 78 and wherein the reflector is flat and is operatively associated with a lens.

81. A method according to claim 80 and wherein the lens is a fresnel lens attached to the reflector.

82. A method according to claim 27 and also comprising providing a light source and a lens operative to provide concentrated light from the light source to at least part of said flat panel display substrate.

83. A method according to claim 82 wherein the projector is situated at a first focus of the lens, and a second focus of the lens is situated away from the flat panel display substrate.

84. A method according to claim 28 and wherein said dark field and said bright field illumination are diffuse.

85. A method according to claim 28 and wherein said dark field and said bright field illumination are focussed.

86. A method according to claim 85 and wherein said surface includes a periodic spatial feature operative to diffract light impinging thereon.

87. A method according to claim 27 and also comprising providing a spatially positionable stage to support the article, wherein the stage spatially positions the article at various angles relative to the illumination subsystem.

88. A method according to claim 87 and wherein the optical array, illumination subsystem and stage are configured and arranged to selectively enable viewing the surface such that a non-zero'th order of diffraction impinges on the staring array camera.

89. A method according to claim 88 and wherein a multiplicity of non-zero'th orders of diffraction of substantially the same order impinge on the staring array camera.

90. A method according to claim 88 and wherein the optical array, the illumination subsystem and the stage are configured and arranged to additionally enable selectively viewing of the surface such that a zero'th order of diffraction impinges on the staring array camera.

91. A method according to claim 88 and wherein the optical array the illumination subsystem and the stage are configured and arranged to additionally enable selectively viewing the object such that substantially no orders of diffraction impinge on the staring array camera.

92. A method according to claim 91 and wherein the optical array, the illumination subsystem and the stage are configured and arranged to sequentially view the object and wherein in one view a selected non-zero order of diffraction impinges on the optical array, and in other sequential views at least one of the following impinges on the optical array: a zero'th order of diffraction, an additional non-zero'th order of diffraction, the same non-zero'th order of diffraction of a different region of the surface of the article, and no order of diffraction.

93. A method according to claim 27 and wherein said optical array views only a part of a surface of said substrate.

94. A method according to any of claim 27 and also comprising providing a light source and a reflector operative to provide concentrated light from the light source to at least part of said surface.

95. A method according to claim 94 wherein said reflector has two points of focus, and wherein a projector is situated at a first focus, and a second focus is situated not on the surface.

96. A method according to claim 95 and wherein the reflector is a section of an ellipsoid.

97. A method according to claim 96 and wherein the reflector is flat and is operatively associated with a lens.

98. A method according to claim 97 and wherein the lens is a fresnel lens attached to the reflector.

99. A method according to claim 27 and also comprising providing a light source and a lens operative to provide concentrated light from the light source to at least part of said flat panel display substrate.

100. A method according to claim 99 providing a projector which is situated at a first focus of the lens, and a second focus of the lens is situated not on the flat panel display substrate.

* * * * *